(12) United States Patent
McDonald et al.

(10) Patent No.: US 9,656,084 B2
(45) Date of Patent: May 23, 2017

(54) SYSTEM AND METHOD FOR ELECTRICAL PULSE CHARGE COMPENSATION FOR IMPLANTABLE MEDICAL DEVICE CAPACITANCE LOADING EFFECTS

(71) Applicant: BOSTON SCIENTIFIC NEUROMODULATION CORPORATION, Valencia, CA (US)

(72) Inventors: Matthew Lee McDonald, Pasadena, CA (US); Joseph M. Bocek, Seattle, WA (US); Thomas W. Stouffer, Chatsworth, CA (US); Robert Graham Lamont, Van Nuys, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 197 days.

(21) Appl. No.: 14/692,582

(22) Filed: Apr. 21, 2015

(65) Prior Publication Data

US 2015/0306399 A1    Oct. 29, 2015

Related U.S. Application Data

(60) Provisional application No. 61/984,699, filed on Apr. 25, 2014.

(51) Int. Cl.
*A61N 1/00* (2006.01)
*A61N 1/36* (2006.01)
(Continued)

(52) U.S. Cl.
CPC ....... *A61N 1/36146* (2013.01); *A61N 1/0551* (2013.01); *A61N 1/36178* (2013.01);
(Continued)

(58) Field of Classification Search
CPC .............. A61N 1/0551; A61N 1/36125; A61N 1/36142; A61N 1/36146; A61N 1/36178; A61N 1/36521; A61N 2001/086
See application file for complete search history.

(56) References Cited

U.S. PATENT DOCUMENTS 6,181,996 B1    1/2001  Chou et al.
6,516,227 B1    2/2003  Meadows et al.
(Continued)

FOREIGN PATENT DOCUMENTS

JP    2012100708    5/2012
WO    2013/013265   1/2013

OTHER PUBLICATIONS

International Search Report and Written Opinion for PCT Application No. PCT/US2015/026938 mailed Jul. 6, 2015.

*Primary Examiner* — Lindsey G Wehrheim
(74) *Attorney, Agent, or Firm* — Lowe Graham Jones PLLC; Bruce E. Black

(57) ABSTRACT

A neurostimulation device and system are provided. At least one neurostimulation lead having a plurality of electrodes is configured for being implanted within tissue of a patient. A shunt capacitance is coupled to one of the electrodes. Time-varying electrical current is delivered to at least one of the electrodes, wherein the shunt capacitance would, without compensation, absorb charge from or inject charge into the tissue in response to time-varying changes in the delivered electrical current, thereby causing an uncompensated electrical waveform to be delivered to the tissue adjacent the one electrode, The absorbed or injected charge is at least partially compensated for, thereby causing a compensated electrical waveform to be delivered to the tissue adjacent the one electrode.

20 Claims, 15 Drawing Sheets

(51) Int. Cl.
*A61N 1/05* (2006.01)
*A61N 1/365* (2006.01)
*A61N 1/08* (2006.01)

(52) U.S. Cl.
CPC ...... *A61N 1/36125* (2013.01); *A61N 1/36142* (2013.01); *A61N 1/36521* (2013.01); *A61N 2001/086* (2013.01)

(56) References Cited

U.S. PATENT DOCUMENTS

| | | |
|---|---|---|
| 6,535,767 B1 | 3/2003 | Kronberg |
| 6,895,280 B2 | 5/2005 | Meadows et al. |
| 7,539,538 B2 | 5/2009 | Parramon et al. |
| 7,650,184 B2 | 1/2010 | Walter |
| 8,019,439 B2 | 9/2011 | Kuzma et al. |
| 8,036,754 B2 | 10/2011 | Lee et al. |
| 2003/0139781 A1 | 7/2003 | Bradley et al. |
| 2006/0200218 A1* | 9/2006 | Wahlstrand .......... A61N 1/0534 607/116 |
| 2009/0216306 A1 | 8/2009 | Barker |
| 2012/0158077 A1* | 6/2012 | Buessing ............... A61N 1/056 607/8 |
| 2012/0290038 A1 | 11/2012 | Moffitt et al. |
| 2013/0204319 A1 | 8/2013 | Trier et al. |

* cited by examiner $E_{case}$ $E_{case}$

SYSTEM AND METHOD FOR ELECTRICAL PULSE CHARGE COMPENSATION FOR IMPLANTABLE MEDICAL DEVICE CAPACITANCE LOADING EFFECTS

CROSS-REFERENCE TO RELATED APPLICATIONS

This application claims the benefit under 35 U.S.C. §119 (e) of U.S. provisional patent application Ser. No. 61/984, 699, filed Apr. 25, 2014, which is incorporated herein by reference.

FIELD OF THE INVENTION

The present invention relates to implantable medical devices, and more particularly, implantable medical devices that compensate for capacitance loading effects.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy. Further, in recent investigations Peripheral Nerve Stimulation (PNS) systems have demonstrated efficacy in the treatment of chronic pain syndromes and incontinence, and a number of additional applications are currently under investigation. Furthermore, Functional Electrical Stimulation (FES) systems such as the Freehand system by NeuroControl (Cleveland, Ohio) have been applied to restore some functionality to paralyzed extremities in spinal cord injury patients.

Each of these implantable neurostimulation systems typically includes at least one stimulation lead implanted at the desired stimulation site and an implantable Pulse Generator (IPG) implanted remotely from the stimulation site, but coupled either directly to the stimulation lead(s) or indirectly to the stimulation lead(s) via one or more lead extensions. Thus, electrical pulses can be delivered from the neurostimulator to the electrodes carried by the stimulation lead(s) to stimulate or activate a volume of tissue in accordance with a set of stimulation parameters and provide the desired efficacious therapy to the patient. A typical stimulation parameter set may include the electrodes that are sourcing (anodes) or returning (cathodes) the stimulation current at any given time, as well as the amplitude, duration, rate, and burst rate of the electrical pulses. Significant to the present inventions described herein, a typical IPG may be manually inactivated by the patient by placing a magnet over the implanted IPG, which closes a reed switch contained within the IPG.

The neurostimulation system may further comprise a handheld Remote Control (RC) to remotely instruct the neurostimulator to generate electrical pulses in accordance with selected stimulation parameters. The RC may, itself, be programmed by a technician attending the patient, for example, by using a Clinician's Programmer (CP), which typically includes a general purpose computer, such as a laptop, with a programming software package installed thereon.

Electrical stimulation energy may be delivered from the neurostimulator to the electrodes using one or more current-controlled sources for providing electrical pulses of a specified and known current (i.e., current regulated output pulses), or one or more voltage-controlled sources for providing electrical pulses of a specified and known voltage (i.e., voltage regulated output pulses). The circuitry of the neurostimulator may also include voltage converters, power regulators, output coupling capacitors, and other elements as needed to produce constant voltage or constant current stimulus pulses.

Neurostimulation systems, which may not be limited to SCS used to treat chronic pain, are routinely implanted in patients who are in need of Magnetic Resonance Imaging (MRI). Thus, when designing implantable neurostimulation systems, consideration must be given to the possibility that the patient in which neurostimulator is implanted may be subjected to electro-magnetic interference generated by MRI scanners, which may potentially cause damage to the neurostimulator as well as discomfort to the patient. Typically, electromagnetic interference (EMI) filters are placed between the ports of the neurostimulators and the tissue contacting electrodes to ensure correct operation and prevent damage to the neurostimulator in environments with high radio frequency (RF) fields, such as MRI-environments. Typically, these filters incorporate capacitors, which shunt the RF energy to a common node, such as the metallic case of the neurostimulator to protect internal circuitry. Additionally, lead inter-conductor capacitances contribute shunting capacitances between the neurostimulator outputs. Another source of shunting capacitance is the capacitance of internal neurostimulator circuit elements, such as active electronic switches disposed for the delivery of electrical pulses.

During the delivery of electrical pulses, the shunting capacitances must be charged to the voltage present on the electrode during the delivery of the electrical pulses. The charge absorbed or delivered from the capacitances alters the wave shape of the delivered electrical pulses on the active electrodes.

For example, normally the neurostimulator drives current into tissue at the electrodes at the end of the neurostimulation leads. Each electrode can be treated as an ideal current source, with the tissue approximated as a resistor network. The total current delivered to the tissue by the electrodes must be equal to zero (i.e., the total magnitude of the anodic current must be equal to the total magnitude of the cathodic current). For example, as illustrated in FIG. 1, the simplest case is an electrical source (in this case, a current source I) between two electrodes, one acting as an anode E1, and the other acting as a cathode (in this case, a case electrode $E_{case}$). Of course, electrode E1 can alternatively be the cathode E1, and the case electrode $E_{case}$ may be the anode. As such, the current flow shown by the arrow of the electrical source illustrated in FIG. 1, as well as the subsequent figures provided in this specification, is arbitrary, and thus, the direction of the arrow represented in the current sources provided herein does not necessarily mean that the current actually flows in that direction.

Thus, electrical current $i_t$, which is equal to the current generated by the current source I, flows through the tissue resistance $R_t$ between the electrode E1 and the case electrode $E_{case}$ (i.e., anodic electrical current enters the tissue from electrode E1 and an cathodic electrical current of equal magnitude exits the tissue into the case electrode $E_{case}$). The voltage V developed across the tissue resistance $R_t$ is described by ohm's law (V=IR). It should be noted that the true circuit includes DC blocking capacitors. However, these DC blocking capacitors are sufficiently large to have negligible voltage change during delivery of an electrical pulse, they are normally ignored for the purposes of analyzing the electrical properties of the stimulation energy, and so are not explicitly shown in the simplified model illustrated in FIG. 1.

However, as discussed above, it is possible for shunt capacitances, such as EMI filters, internal stimulation circuitry capacitances, and lead inter-conductor capacitances, to have parasitic components that do distort the stimulation enough to be of concern. An example of such a circuit is illustrated in FIG. 2, where C1, R1, and C2 represent lumped element models of the parasitic components of the neurostimulation lead, and any shunt capacitances in EMI filters and internal stimulation circuitry between two electrodes, one acting as a cathode E1, and the other acting as an anode (in this case, a case electrode $E_{case}$). Current $i_1$ and $i_2$ will leak through the shunt capacitances C1 and C2 in response to changes in the voltage across these capacitances, preventing the specified electrical drive current I from reaching the tissue, modeled as $R_t$. Instead, current $i_t$ flows through the tissue resistance $R_t$.

This shunting phenomenon alters the shape of each electrical pulse, and thus, the waveshape of the current delivered to the tissue of the patient. In the case where the stimulation source approximates a voltage source, the total charge delivered to the patient may also be altered. For example, the rise time of the electrical pulse current may be increased while the capacitances connected to the active electrodes are charging. For example, as shown in FIG. 3, the ideal electrical pulse current has a relatively short rise time, whereas the actual electrical pulse current due to the absorption of charge from the capacitances has a relatively long rise time. Although the ideal electrical pulse is shown as being square, in reality, the electrical pulse current will have a nominally trapezoidal wave shape, with the current flowing in the shunting capacitances during the rising and falling edges of the pulse.

In either event, this will result in an unintended change in the total charge delivered to the tissue during the electrical pulse. Further, inactive electrodes may also be subject to voltage shifts during the delivery of the electrical pulse due to their contact with tissue near the stimulation site, resulting in changes in the charge level of the capacitors connected to these electrodes. The change in charge may result in unintended delivery or removal of charge at the associated tissue-contacting electrode and unintended changes in polarization of this tissue, or even unintended tissue stimulation.

There, thus, remains a need to compensate for changes in charge at tissue-contacting electrodes due to shunt capacitances in the stimulation circuit.

SUMMARY OF THE INVENTION

In accordance with a first aspect of the present inventions, a neurostimulation device comprises a plurality of electrical terminals configured for being respectively coupled to a plurality of stimulation electrodes implanted within tissue of a patient, and stimulation output circuitry configured for delivering time-varying electrical current to at least one of the electrodes via the respective electrical terminal(s). The stimulation output circuitry includes a shunt capacitance (e.g., at least one of an electromagnetic interference (EMI) capacitance and a lead capacitance) coupled to one of the electrodes via the respective one electrical terminal that would, without compensation, absorb charge from or inject charge into the tissue in response to time-varying changes in the delivered electrical current, thereby causing an uncompensated electrical waveform to be delivered to the tissue adjacent the one electrode. In one embodiment, the delivered electrical stimulation energy comprises pulsed electrical energy having an electrical pulse having a rising edge and a failing edge, in which case, the shunt capacitance would, without compensation, absorb charge from the tissue in response to a rising edge of the electrical pulse, and inject charge into the tissue in response to a falling edge of the electrical pulse.

The neurostimulation device further comprises a controller configured for directing the stimulation output circuitry to at least partially compensate for the absorbed or injected charge, thereby causing a compensated electrical waveform to be delivered to the tissue adjacent the one electrode. The electrode to which the compensated electrical waveform is delivered may be one of the electrode(s) to which the time-varying electrical current is delivered or may be an electrode that may not be one of the electrode(s) to which the time-varying electrical current is delivered. The neurostimulation device may optionally comprise memory configured for storing a programmed electrical parameter (e.g., an electrical current value) defining a characteristic of the desired electrical waveform. The neurostimulation device may further comprise telemetry circuitry configured for receiving the programmed electrical parameter from an external controller. The neurostimulation device may further comprise a housing containing the plurality of electrical terminals, stimulation output circuitry, and controller.

In one embodiment, a characteristic between the uncompensated electrical waveform and a desired electrical waveform has a first error value (which may be substantial), and the same characteristic between the compensated electrical waveform and the desired electrical waveform has a second error value less than the first error value (which may be insubstantial). The desired electrical waveform may be a null electrical waveform. The characteristic may be a total electrical charge over a period of time. The characteristic may be a total electrical charge over a period of time, a magnitude of an electrical current in a period of time (e.g., an average electrical current over the period of time), or waveform shape. In the latter case, the waveform shape of the compensated electrical waveform matches the waveform shape of the desired electrical waveform more than the uncompensated electrical waveform matches the waveform shape of the desired electrical waveform.

In another embodiment, the stimulation output circuitry includes another shunt capacitance coupled to another one of the electrodes via the respective other electrical terminal that would, without compensation, absorb charge from or inject charge into the tissue in response to time-varying changes in the delivered electrical energy, thereby causing another uncompensated electrical waveform to be delivered to the tissue adjacent the other one electrode, and the controller is further configured for directing the stimulation output circuitry to at least partially compensate for the absorbed or injected charge, thereby causing another compensated electrical waveform to be delivered to the tissue adjacent the other one electrode.

In still another embodiment, the controller is configured for directing the stimulation output circuitry to at least partially compensate for the absorbed or injected charge by actively injecting charge into the shunt capacitance if the shunt capacitance would, without compensation, remove charge from the tissue, and/or actively removing charge from the shunt capacitance if the shunt capacitance would, without compensation, inject charge into the tissue.

In yet another embodiment, the stimulation output circuitry comprises an electrical source configured for being coupled to the one electrode via the respective one electrical terminal, and the controller is configured for directing the electrical source to at least partially compensate for the absorbed or injected charge by generating an electrical current. The electrical current source may have an arbitrary pulse shaping capability that is controllable by the controller. The neurostimulation device may further comprise a processor configured for computing the value of the electrical current generated by the electrical source based on a differential equation that is a function of the shunt capacitance and the desired electrical current value. The neurostimulation device may further comprise a sensing device configured for measuring a change in a voltage at the one electrode during the delivery of the time-varying electrical current, and a processor configured for computing the magnitude and polarity of electrical current flowing through the tissue adjacent the one electrode based on the measured voltage change, computing a magnitude and polarity of a compensating electrical current based on the computed magnitude and polarity of the electrical current flowing through the tissue adjacent the one electrode and the desired electrical current value, and adding a function of the magnitude and polarity of the compensated electrical current to the desired electrical current value to obtain a magnitude and polarity of the electrical current that the controller directs the electrical source to generate. The function may be, e.g., one of a gain, a differentiation of the compensating electrical current over time multiplied by a gain, and an integration of the compensating electrical current over time multiplied by a gain.

In accordance with a second aspect of the present invention, a neurostimulation system comprises at least one neurostimulation lead having a plurality of electrodes configured for being implanted within tissue of a patient, a shunt capacitance (e.g., at least one of an electromagnetic interference (EMI) capacitance and a lead capacitance) coupled to one of the electrodes, and a neurostimulation device configured for delivering time-varying electrical current to at least one of the electrodes, wherein the shunt capacitance would, without compensation, absorb charge from or inject charge into the tissue in response to time-varying changes in the delivered electrical current, thereby causing an uncompensated electrical waveform to be delivered to the tissue adjacent the one electrode. In one embodiment, the delivered electrical stimulation energy comprises pulsed electrical energy having an electrical pulse having a rising edge and a falling edge, in which case, the shunt capacitance would, without compensation, absorb charge from the tissue in response to a rising edge of the electrical pulse, and inject charge into the tissue in response to a falling edge of the electrical pulse.

The neurostimulation device is further configured for at least partially compensating for the absorbed or injected charge, thereby causing a compensated electrical waveform to be delivered to the tissue adjacent the one electrode. The electrode to which the compensated electrical waveform is delivered may be one of the electrode(s) to which the time-varying electrical current is delivered or may be an electrode that may not be one of the electrode(s) to which the time-varying electrical current is delivered. The neurostimulation device may optionally be configured for storing a programmed electrical parameter (e.g., an electrical current value) defining a characteristic of the desired electrical waveform. The neurostimulation device may further be configured for receiving the programmed electrical parameter from an external controller.

In one embodiment, a characteristic between the uncompensated electrical waveform and a desired electrical waveform has a first error value (which may be substantial), and the same characteristic between the compensated electrical waveform and the desired electrical waveform has a second error value less than the first error value (which may be insubstantial). The desired electrical waveform may be a null electrical waveform. The characteristic may be a total electrical charge over a period of time. The characteristic may be a total electrical charge over a period of time, a magnitude of an electrical current in a period of time (e.g., an average electrical current over the period of time), or waveform shape. In the latter case, the waveform shape of the compensated electrical waveform matches the waveform shape of the desired electrical waveform more than the uncompensated electrical waveform matches the waveform shape of the desired electrical waveform.

In another embodiment, the neurostimulation device further comprises another shunt capacitance coupled to another one of the electrodes that would, without compensation, absorb charge from or inject charge into the tissue in response to time-varying changes in the delivered electrical energy, thereby causing another uncompensated electrical waveform to be delivered to the tissue adjacent the other one electrode. In this case, the neurostimulation device is further configured for at least partially compensating for the absorbed or injected charge, thereby causing another compensated electrical waveform to be delivered to the tissue adjacent the other one electrode.

In still another embodiment, the neurostimulation device is configured for at least partially compensating for the absorbed or injected charge by actively injecting charge into the shunt capacitance if the shunt capacitance would, without compensation, remove charge from the tissue, and/or actively removing charge from the shunt capacitance if the shunt capacitance would, without compensation, inject charge into the tissue.

In yet another embodiment, the neurostimulation device comprises an electrical source configured for being coupled to the one electrode, and the neurostimulation device is configured for directing the electrical source to at least partially compensate for the absorbed or injected charge by generating an electrical current. The electrical current source may have an arbitrary pulse shaping capability that is controllable by the controller. The neurostimulation device may be further configured for computing the value of the electrical current generated by the electrical source based on a differential equation that is a function of the shunt capacitance and the desired electrical current value. The neurostimulation device may further comprise a sensing device configured for measuring a change in a voltage at the one electrode during the delivery of the time-varying electrical current. In this case, the neurostimulation device may further be configured for computing the magnitude and polarity of electrical current flowing through the tissue adjacent the one electrode based on the measured voltage change, computing a magnitude and polarity of a compensating electrical current based on the computed magnitude and polarity of the electrical current flowing through the tissue adjacent the one electrode and the desired electrical current value, and adding a function of the magnitude and polarity of the compensated electrical current to the desired electrical current value to obtain a magnitude and polarity of the electrical current that the controller directs the electrical source to generate. The function may be, e.g., one of a gain, a differentiation of the compensating electrical current over time multiplied by a gain, and an integration of the compensating electrical current over time multiplied by a gain.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

The description that follows relates to a spinal cord stimulation (SCS) system. However, it is to be understood that while the invention lends itself well to applications in SCS, the invention, in its broadest aspects, may not be so limited. Rather, the invention may be used with any type of implantable electrical circuitry used to stimulate tissue. For example, the present invention may be used as part of a multi-lead system such as a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neural stimulator configured to treat urinary incontinence, sleep apnea, shoulder sublaxation, headache, etc.

Figure 4:
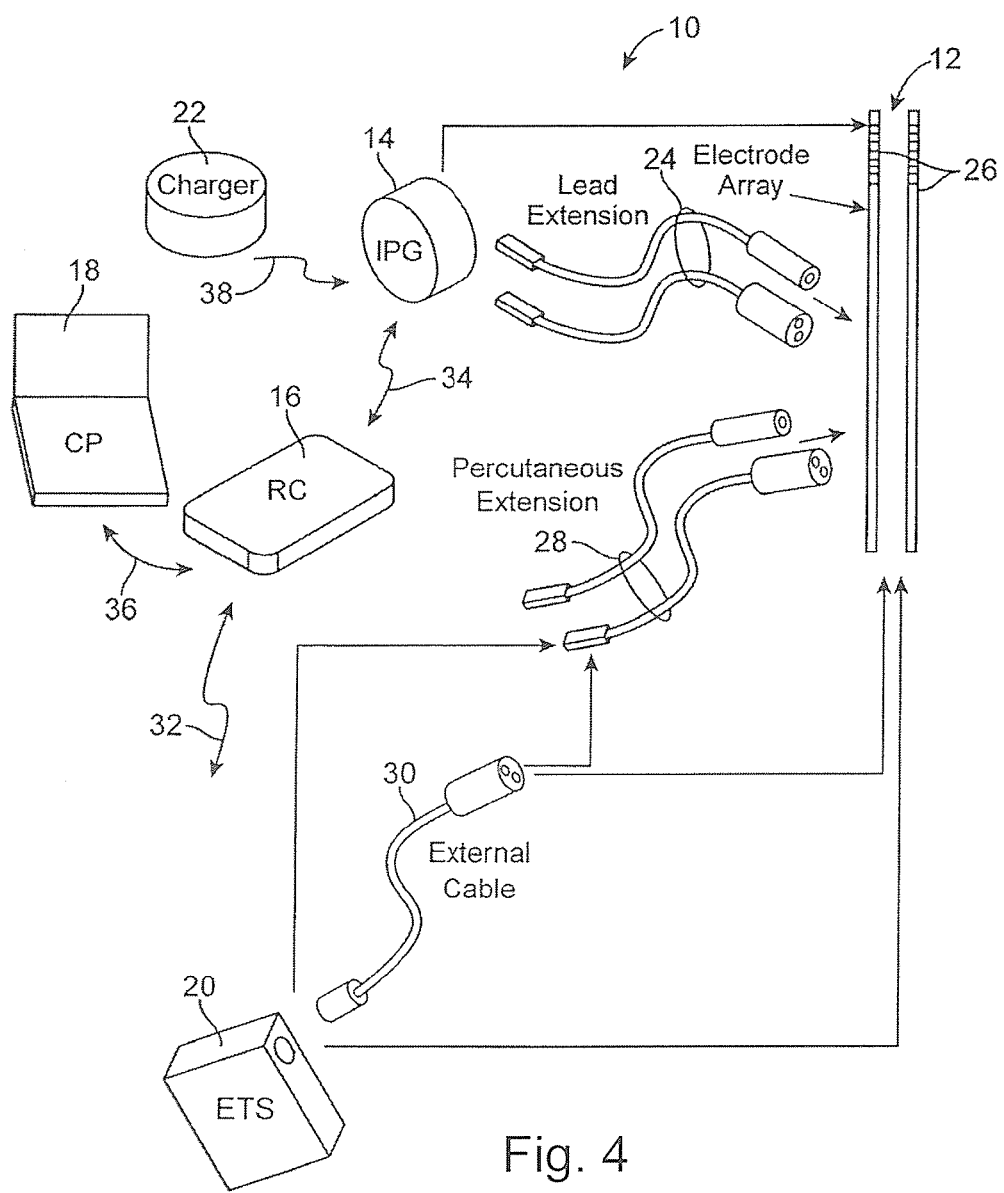
FIG. 4 is a plan view of a Spinal Cord Stimulation (SCS) system constructed in accordance with one embodiment of the present inventions.

Turning first to FIG. 4, an exemplary SCS system 10 generally comprises a plurality of neurostimulation leads 12 (in this case, two percutaneous leads), an implantable pulse generator (IPG) 14, an external remote control (RC) 16, a Clinician's Programmer (CP) 18, an External Trial Stimulator (ETS) 20, and an external charger 22.

The IGP 14 is physically connected via two lead extensions 24 to the neurostimulation leads 12, which carry a plurality of electrodes 26 arranged in an array. In the illustrated embodiment, the neurostimulation leads 12 are percutaneous leads, and to this end, the electrodes 26 are arranged in-line along the neurostimulation leads 12. The number of neurostimulation leads 12 illustrated is two, although any suitable number of neurostimulation leads 12 can be provided, including only one. Alternatively, a surgical paddle lead can be used in place of one or more of the percutaneous leads. As will also be described in further detail below, the IGP 14 includes pulse generation circuitry that delivers electrical stimulation energy in the form of a pulsed electrical waveform (i.e., a temporal series of electrical pulses) to the electrode array 26 in accordance with a set of stimulation parameters. The IGP 14 and neurostimulation leads 12 can be provided as an implantable neurostimulation kit, along with, e.g., a hollow needle, a stylet, a tunneling tool, and a tunneling straw. Further details discussing implantable kits are disclosed in U.S. Application Ser. No. 61/030,506, entitled "Temporary Neurostimulation Lead Identification Device," which is expressly incorporated herein by reference.

The ETS 20 may also be physically connected via percutaneous lead extensions 28 or external cable 30 to the neurostimulation lead 12. The ETS 20, which has similar pulse generation circuitry as the IGP 14, also delivers electrical stimulation energy in the form of a pulsed electrical waveform to the electrode array 26 in accordance with a set of stimulation parameters. The major difference between the ETS 20 and the IGP 14 is that the ETS 20 is a non-implantable device that is used on a trial basis after the neurostimulation lead 12 has been implanted and prior to implantation of the IGP 14, to test the responsiveness of the stimulation that is to be provided. Thus, any functions described herein with respect to the IGP 14 can likewise be performed with respect to the ETS 20.

The RC 16 may be used to telemetrically control the ETS 20 via a bi-directional RF communications link 32. Once the IGP 14 and stimulation leads 12 are implanted, the RC 16 may be used to telemetrically control the IGP 14 via a bi-directional RF communications link 34. Such control allows the IGP 14 to be turned on or off and to be programmed with different stimulation programs after implantation. Once the IGP 14 has been programmed, and its power source has been charged or otherwise replenished, the IGP 14 may function as programmed without the RC 16 being present.

The CP 18 provides clinician detailed stimulation parameters for programming the IGP 14 and ETS 20 in the operating room and in follow-up sessions. The CP 18 may perform this function by indirectly communicating with the IGP 14 or ETS 20, through the RC 16, via an IR communications link 36. Alternatively, the CP 18 may directly communicate with the IGP 14 or ETS 20 via an RF communications link (not shown).

The external charger 22 is a portable device used to transcutaneously charge the IGP 14 via an inductive link 38. Once the IGP 14 has been programmed, and its power source has been charged by the external charger 22 or otherwise replenished, the IGP 14 may function as programmed without the RC 16 or CP 18 being present.

For the purposes of this specification, the terms "neurostimulator," "stimulator," "neurostimulation," and "stimulation" generally refer to the delivery of electrical energy that affects the neuronal activity of neural tissue, which may be excitatory or inhibitory; for example by initiating an action potential, inhibiting or blocking the propagation of action potentials, affecting changes in neurotransmitter/neuromodulator release or uptake, and inducing changes in neuroplasticity or neurogenesis of tissue. For purposes of brevity, the details of the CP 18, ETS 20, and external charger 22 will not be described herein. Details of exemplary embodiments of these components are disclosed in U.S. Pat. No. 6,895,280, which is expressly incorporated herein by reference.

Figure 5:
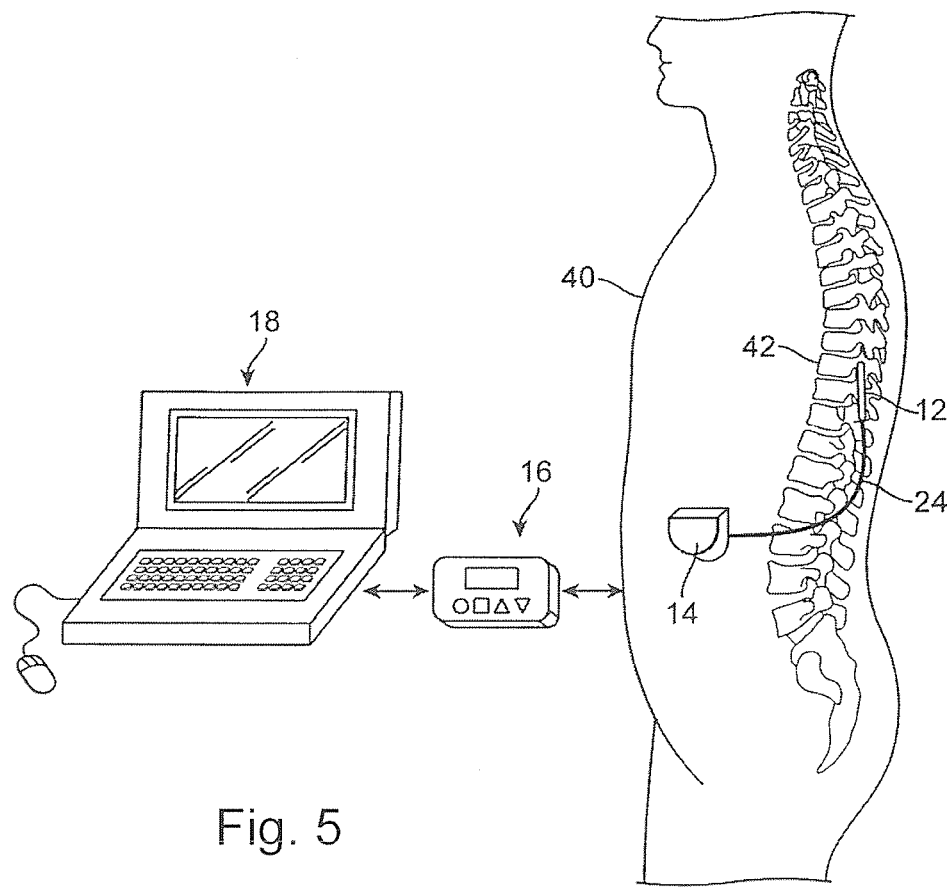
FIG. 5 is a plan view of the SCS system of FIG. 4 in use within a patient.

Referring to FIG. 5, the neurostimulation leads 12 are implanted at an initial position within the spinal column 42 of a patient 40. The preferred placement of the neurostimulation leads 12 is adjacent, i.e., resting near, or upon the dura, adjacent to the spinal cord area to be stimulated. Due to the lack of space near the location where the neurostimulation leads 12 exit the spinal column 42, the IGP 14 is generally implanted in a surgically-made pocket either in the abdomen or above the buttocks. The IGP 14 may, of course, also be implanted in other locations of the patient's body. The lead extensions 24 facilitate locating the IGP 14 away from the exit point of the neurostimulation leads 12. As there shown, the CP 18 communicates with the IGP 14 via the RC 16. After implantation, the IGP 14 can be operated to generate a volume of activation relative to the target tissue to be treated, thereby providing the therapeutic stimulation under control of the patient.

Figure 6:
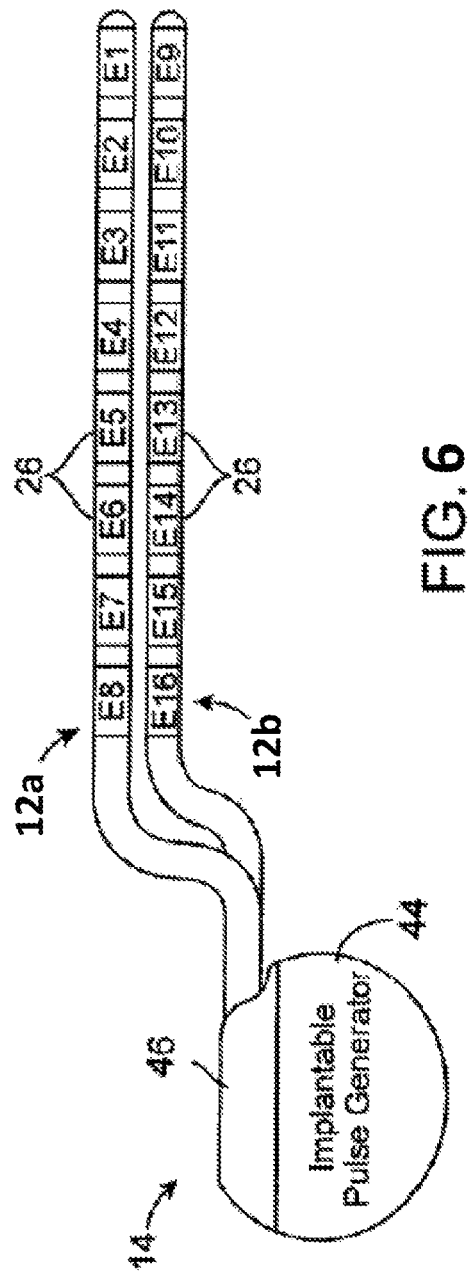
FIG. 6 is a plan view of an implantable pulse generator (IPG) and two percutaneous stimulation leads used in the SCS system of FIG. 4.

Referring now to FIG. 6, the external features of the neurostimulation leads 12*a*, 12*b* and the IGP 14 will be briefly described. Each of the neurostimulation leads 12 has eight electrodes 26 (respectively labeled E1-E8 for the lead 12*a* and E9-E16 for the lead 12*b*). The actual number and shape of leads and electrodes will, of course, vary according to the intended application. Further details describing the construction and method of manufacturing percutaneous stimulation leads are disclosed in U.S. patent application Ser. No. 11/689,918, entitled "Lead Assembly and Method of Making Same," and U.S. patent application Ser. No. 11/565,547, entitled "Cylindrical Multi-Contact Electrode Lead for Neural Stimulation and Method of Making Same," the disclosures of which are expressly incorporated herein by reference.

The IGP 14 comprises an outer case 44 for housing the electronic and other components (described in further detail below). The outer case 44 is composed of an electrically conductive, biocompatible material, such as titanium, and forms a hermetically sealed compartment wherein the internal electronics are protected from the body tissue and fluids. In some cases, the outer case 44 may serve as an electrode. The IGP 14 further comprises a connector 46 to which the proximal ends of the neurostimulation leads 12 mate in a manner that electrically couples the electrodes 26 to the internal electronics (described in further detail below) within the outer case 44. To this end, the connector 46 includes two ports (not shown) for receiving the proximal ends of the leads 12. In the case where the lead extensions 24 are used, the ports may instead receive the proximal ends of such lead extensions 24.

As briefly discussed above, the IGP 14 includes circuitry that provides electrical stimulation energy to the electrodes 26 in accordance with a set of parameters. Such stimulation parameters may comprise electrode combinations, which define the electrodes that are activated as anodes (positive), cathodes (negative), and turned off (zero), percentage of stimulation energy assigned to each electrode (fractionalized electrode configurations), and electrical pulse parameters, which define the pulse amplitude (measured in milliamps or volts depending on whether the IGP 14 supplies constant current or constant voltage to the electrode array 26), pulse width (measured in microseconds), pulse rate (measured in pulses per second), and burst rate (measured as the stimulation on duration X and stimulation off duration Y). As will be described in further detail below, the IGP 14 also includes circuitry that provides electrical signals, and measured electrical impedance in response to the electrical signals.

With respect to the pulsed electrical waveform provided during operation of the SCS system 10, electrodes that are selected to transmit or receive electrical energy are referred to herein as "activated," while electrodes that are not selected to transmit or receive electrical energy are referred to herein as "non-activated." Electrical energy delivery will occur between two (or more) electrodes, one of which may be the IPG case 44, so that the electrical current has a path from the energy source contained within the IPG case 44 to the tissue and a sink path from the tissue to the energy source contained within the case. Electrical energy may be transmitted to the tissue in a monopolar or multipolar (e.g., bipolar, tripolar, etc.) fashion.

Monopolar delivery occurs when a selected one or more of the lead electrodes 26 is activated along with the case 44 of the IGP 14, so that electrical energy is transmitted between the selected electrode 26 and case 44. Monopolar delivery may also occur when one or more of the lead electrodes 26 are activated along with a large group of lead electrodes located remotely from the one or more lead electrodes 26 so as to create a monopolar effect; that is, electrical energy is conveyed from the one or more lead electrodes 26 in a relatively isotropic manner. Bipolar delivery occurs when two of the lead electrodes 26 are activated as anode and cathode, so that electrical energy is transmitted between the selected electrodes 26. Tripolar delivery occurs when three of the lead electrodes 26 are activated, two as anodes and the remaining one as a cathode, or two as cathodes and the remaining one as an anode.

Significant to the present inventions, in response to the delivery of the electrical stimulation current to at least one of the electrodes 26 by the neurostimulation system 10, any shunt capacitances, without compensation, may absorb charge from or inject charge into the tissue, thereby causing an uncompensated electrical waveform to be delivered to the tissue adjacent any one or more electrodes 26. In the illustrated embodiment, the uncompensated electrical waveform delivered to the tissue adjacent the electrode(s) 26 as a result of the shunting of the electrical current through the shunt capacitances is substantially different from a desired electrical waveform. For the purposes of this specification, an uncompensated electrical waveform actually delivered to electrode(s) 26 is substantially different from a desired electrical waveform for those electrode(s) 26 if it provides a clinical effect that differs from the clinical effect that would have been provided if the desired electrical waveform were actually delivered to the electrode(s) 26 (e.g., the patient may experience less therapy if the shunt capacitance(s) shunt electrical current away from the stimulation electrode or the patient may experience discomfort if the shunt capacitance(s) shunt electrical current toward an inactive electrode).

The neurostimulation system 10 compensates for the absorbed or injected charge, thereby causing a compensated electrical waveform to be delivered to the tissue adjacent the electrode(s). In the illustrated embodiment, the compensated electrical waveform delivered to the tissue adjacent the electrode(s) 26 is substantially the same as a desired electrical waveform for those electrode(s) 26. For the purposes of this specification, a compensated electrical waveform actually delivered to the electrode(s) 26 is substantially equal to the desired electrical waveform for those electrode(s) 26 if it provides a clinical effect that does not differ from the clinical effect that would have been provided if the desired electrical waveform actually delivered to the electrode(s) 26 (e.g., despite the compensation function, the patient may experience the same therapy if the shunt capacitance(s) shunt an insignificant amount of electrical current away from the stimulation electrode or the patient may not experience discomfort if the shunt capacitance(s) shunt an insignificant amount of electrical current towards inactive electrode).

The neurostimulation system 10 may store a programmed electrical parameter (e.g., an electrical value or even a pulse shape) that defines the characteristic of the desired electrical waveform. For example, neurostimulation system 10 may be programmed with an electrical current value for a particular electrode that ultimately defines the desired average electrical current or total electrical charge over the rising edge of the electrical pulse delivered by that electrode. Typically, the desired average electrical current should equal the programmed electrical current value, or the desired total charge over the rising edge of the electrical pulse should equal the programmed electrical current value times the duration of the rising edge of the electrical pulse.

The uncompensated and compensated electrical waveforms can best be quantified in terms of error values relative to a desired electrical waveform. In particular, a characteristic, such as, e.g., an average electrical current, total electrical charge, or a waveform shape over a period of time (e.g., over the rising edge of the electrical pulse) between the uncompensated electrical waveform and a desired electrical waveform may have a first error value, and the same characteristic between the compensated electrical waveform and the desired electrical waveform has a second error value less than the first error value.

As previously discussed, the characteristic of the electrical waveform to be compensated for may be an average current. For example, if electrode E1 is programmed to deliver a cathodic electrical current having a desired value of −1 mA, shunting of electrical current through the shunt capacitances may cause an uncompensated cathodic electrical current having an average value of −1.5 mA to be delivered to electrode E1 during the rising edge of the electrical pulse, thereby yielding an error value of 0.5 mA for electrode E1. However, the compensated cathodic electrical current for electrode E1 may be −0.8 mA during the rising edge of the electrical pulse, thereby yielding an error value of 0.2 mA, which is less than the uncompensated error value of 0.5 mA.

As another example, if electrode E2 is programmed to deliver no electrical current (i.e., an electrical current having a zero value) (in other words, a null waveform), shunting of electrical current though the shunt capacitances may cause an uncompensated anodic electrical current having an average value of +0.2 mA to be delivered to electrode E2 during the rising edge of the electrical pulse, thereby yielding an error value value of 0.2 mA for electrode E2. However, the compensated electrical current for electrode E1 may be −0.05 mA, thereby yielding an error value of 0.05 mA, which is less than the uncompensated error value of 0.2 mA.

As previously discussed, the characteristic of the electrical waveform to be compensated for may be a total electrical charge. For example, if electrode E1 is programmed to deliver cathodic electrical current having a value of −1 mA, which may translate to a total charge of −50 pC over a 50 μs initial time period of an ideally square electrical pulse, shunting of electrical current through the shunt capacitances may cause an uncompensated total charge of −35 pC to be delivered to electrode E1 during a 50 μs rising edge of the electrical pulse, thereby yielding an error value of 15 pC for electrode E1. However, the compensated total electrical charge for electrode E1 during the 50 μs rising edge of the electrical pulse may be −40 pC, thereby yielding an error value of 10 pC, which is less than the uncompensated error value of 15 pC.

As another example, if electrode E2 is programmed to deliver no electrical current (i.e., an electrical current having a zero value), shunting of electrical current though the shunt capacitances may cause an uncompensated total electrical charge of 10 pC to be delivered to electrode E2 during a 50 μs rising edge of the electrical pulse, thereby yielding an error value of 10 pC for electrode E2. However, the compensated total electrical charge for electrode E1 during the 50 μs rising edge of the electrical pulse may be −5 pC, thereby yielding an error value of 2.5 pF, which is less than the uncompensated error value of 10 pF.

As previously discussed, the characteristic of the electrical waveform to be compensated for may be a waveform shape. For example, if electrode E1 is programmed to deliver a trapezoidal electrical pulse with a relatively steep rising edge, shunting of electrical current through the shunt capacitances may cause electrical pulse having a relatively shallow rising edge to be delivered to electrode E1, thereby causing a substantial mismatch between the waveform shape of the electrical pulse actually delivered to electrode E1 and the waveform shape of the ideal electrical pulse. However, the compensated waveform shape for electrode E1 during the rising edge of the electrical pulse may better match the relatively steep rising edge of the programmed b electrical pulse.

Matching between the uncompensated or compensated waveform shape and the ideal waveform shape can be performed using any one of a variety of comparison functions, such as a Pearson Correlation Coefficient function or a least squares based function, which yield error coefficients.

Regardless of the characteristic of the electrical waveform for which compensation is performed, the neurostimulation system 10 provides for the active injection or removal of charge to each of the electrodes 26 to perform such compensation function. The charge injection or removal may be timed to coincide with the change in charge cumulative shunt capacitance; that is, cumulative current flow in the shunt capacitances, due to the electrical pulse delivery, so as to cancel or minimize the change in charge delivery to the tissue due to the loading effects of the shunting capacitors. Partial cancellation of the shunting currents may be accomplished by injecting an equal and opposite level of current onto the respective shunting capacitors using active injection from other internal IPG circuits. The active injection or removal of charge may be accomplished by additional circuitry provided for this purpose, or may be accomplished using existing stimulation circuitry.

Perfect cancellation is generally not possible but it is also not required. It is sufficient to reduce the unintended change in charge delivered to the tissue as a function of time to levels that do not have a physiological impact. For example, for electrodes programmed to be inactive, if charge balance in tissue contacted by an electrode is maintained over a period much smaller (e.g., a factor of 10 lower) than the chronaxie of the tissue, such that the charge balance during the period never reaches minimum levels to stimulate tissue, then the possibility of tissue stimulation may be minimized, even if perfect cancellation during the period is not achieved.

Figure 7:
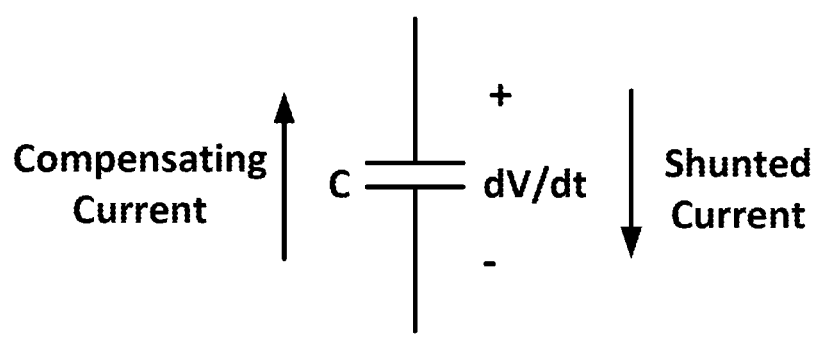
FIG. 7 is a circuit diagram of a shunting capacitor through which a current may flow in response to a change in voltage across the capacitor.

As an example illustrated in FIG. 7, to compensate for the shunt capacitances, if a shunt capacitance has a value of 1 nF, and the electrical pulse rising edge results in a change of 3V across the shunt capacitance, then charge of 3 nC would be injected into the shunt capacitance to compensate for this voltage increase. This charge value can be computed using the capacitor charge and voltage equation: Q=CV (where Q is the shunt capacitance charge, C is the shunt capacitance value, and V is the voltage across the shunt capacitance). The compensating current may be computed using the formula I=C*dV/dt (where I is the current through the shunt capacitance, C is the shunt capacitance value, and dV/dt is the rate of change of voltage across the shunt capacitance. For example, if the rise time of the electrical pulse to the 3V level is 5 µs, then a compensating current of 600 µA would be injected into the shunt capacitance during the rising edge of the electrical pulse. Similar considerations apply to the falling edge of the electrical pulse (in which case, a shunt capacitance would deliver a charge) or during other periods with the amplitude of the electrical pulse is changing. For driven electrodes (i.e., electrodes programmed as active), the actual current delivered will be equal to the compensating current and the programmed stimulation current. For non-driven electrodes (i.e., electrodes programmed to be inactive), the actual current delivered will be equal to the compensating current.

Figure 8:
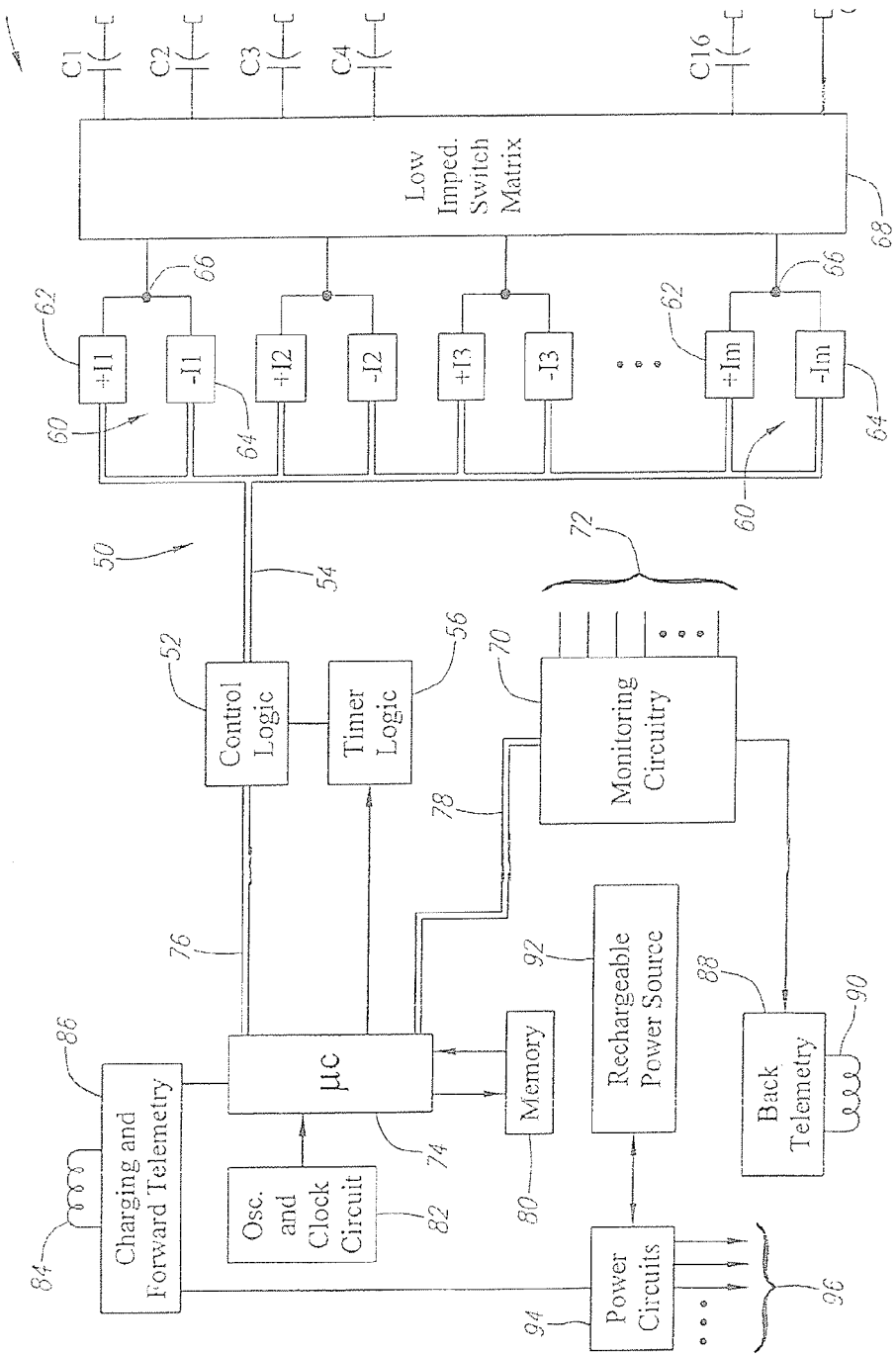
FIG. 8 is a block diagram of the internal components of the IPG of FIG. 6.

Turning next to FIG. 8, the main internal components of the IGP 14 will now be described. The IGP 14 includes stimulation output circuitry 50 configured for generating electrical stimulation energy in accordance with a defined pulsed waveform having a specified pulse amplitude, pulse rate, pulse width, pulse shape, and burst rate under control of control logic 52 over data bus 54. Control of the pulse rate and pulse width of the electrical waveform is facilitated by timer logic circuitry 56, which may have a suitable resolution, e.g., 10 µs. The stimulation energy generated by the stimulation output circuitry 50 is output via capacitors C1-C16 to electrical terminals 58 corresponding to the electrodes 26.

The stimulation output circuitry 50 may comprise one or more independently controlled electrical sources, which take the form of anodic current sources and/or cathodic current sources (sinks), for providing electrical pulses of a specified and known amperage to or from the electrodes 26. The current sources include constant current sources and associated analog switches to generate the electrical pulse trains.

For example, the stimulation output circuitry 50 may comprise a plurality m independent current source pairs 60 capable of supplying stimulation energy to the electrical terminals 58 at a specified and known amperage. One current source 62 of each pair 60 functions as a positive (+) or anodic current source, while the other current source 64 of each pair 60 functions as a negative (−) or cathodic current source. The outputs of the anodic current source 62 and the cathodic current source 64 of each pair 60 are connected to a common node 66. The stimulation output circuitry 50 further comprises a low impedance switching matrix 68 through which the common node 66 of each current source pair 60 is connected to any of the electrical terminals 58 via the capacitors C1-C16.

Thus, for example, it is possible to program the first anodic current source 62 (+I1) to produce a pulse having a peak amplitude of +4 mA (at a specified rate and for a specified duration), and to synchronously program the second cathodic current source 64 (−I2) to similarly produce a pulse having a peak amplitude of −4 mA (at the same rate and pulse width), and then connect the node 86 of the anodic current source 62 (+I1) to the electrical terminal 58 corresponding to electrode E3, and connect the node 66 of the cathodic current source 64 (−I2) to the electrical terminal 58 corresponding to electrode E1 In alternative embodiments, rather than utilizing current sources, voltage sources with low impedance series resistances (e.g., 100 ohms or less) can be used to supply the anodic or cathodic electrical current.

Hence, it is seen that each of the programmable electrical terminals 58 can be programmed to have a positive (sourcing current), a negative (sinking current), or off (no current) polarity. Further, the amplitude of the current pulse being sourced or sunk from a given electrical terminal 58 may be programmed to one of several discrete levels. In one embodiment, the current through each electrical terminal 58 can be individually set from 0 to ±10 mA in steps of 100 µA, within the output voltage/current requirements of the IGP 14. Additionally, in one embodiment, the total current output by a group of electrical terminals 58 can be up to ±20 mA (distributed among the electrodes included in the group).

Also, the pulse duration of the current pulses is preferably adjustable in convenient increments, e.g., from 0 to 1 milliseconds (ms) in increments of 10 microseconds (µs). Similarly, the pulse rate is preferably adjustable within acceptable limits, e.g., from 0 to 10,000 pulses per second (pps). Other programmable features can include slow start/end ramping, burst stimulation cycling (on for X time, off for Y time), interphase (i.e., the duration between first and second phases of biphasic energy), and open or closed loop sensing modes. Moreover, it is seen that each of the electrical terminals 58 can operate in a multipolar mode, e.g., where two or more electrical terminals are grouped to source/sink current at the same time. Alternatively, each of the electrical terminals 58 can operate in a monopolar mode where, e.g., the electrical terminals 58 are configured as cathodes (negative), and case of the IGP 14 is configured as an anode (positive).

It can be appreciated that an electrical terminal 58 may be assigned an amplitude and included with any of up to k possible groups, where k is an integer corresponding to the number of channels, and in one embodiment, is equal to 4, and with each channel k having a defined pulse amplitude, pulse width, pulse rate, and pulse shape. Other channels may be realized in a similar manner. Thus, each channel identifies which electrical terminals 58 (and thus electrodes 26) are selected to synchronously source or sink current, the pulse amplitude at each of these electrical terminals, and the pulse width, pulse rate, and pulse shape.

In one embodiment, each of the current sources 62/64 has an arbitrary pulse shaping capability. For example, the shape of each electrical pulse output by each current source 62/64 can be formed of a stepwise function of amplitude levels. In another embodiment, rather than forming the pulse waveform using a stepwise function of amplitude levels, the output stimulation circuitry 50 may include one or more analog circuits that are configured to shape the electrical pulse output by each current source 62/64. Further details discussing pulse shaping are described in U.S. Pat. No. 8,036,754, which is expressly incorporated herein by reference. Further details discussing the selective coupling of current sources to any of the electrodes 26 via a low-impedance switching matrix, as described in U.S. Pat. No. 6,516,227, which is expressly incorporated herein by reference. Alternatively, each electrode can be coupled to a dedicated current source, which allows the electrode to either operate as a current source or a current sink, as described in U.S. Pat. No. 6,181,996, which is expressly incorporated herein by reference.

The IGP 14 further comprises monitoring circuitry 70 for monitoring the status of various nodes or other points 72 throughout the IGP 14, e.g., power supply voltages, temperature, battery voltage, and the like. The monitoring circuitry 70 is also configured for measuring electrical parameter data (e.g., electrode impedance and/or electrode field potential). The IGP 14 further comprises processing circuitry in the form of a microcontroller (µC) 74 that controls the control logic 52 over data bus 76, and obtains status data from the monitoring circuitry 70 via data bus 78. The IGP 14 additionally controls the timer logic 56. The IGP 14 further comprises memory 80 and oscillator and clock circuit 72 coupled to the microcontroller 74. The microcontroller 74, in combination with the memory 80 and oscillator and clock circuit 72, thus comprise a microprocessor system that carries out a program function in accordance with a suitable program stored in the memory 80. The program stored in the memory 80 comprises a set of stimulation parameters, including electrical current values for each of the electrodes 26. Alternatively, for some applications, the function provided by the microprocessor system may be carried out by a suitable state machine.

Thus, the microcontroller 74 generates the necessary control and status signals, which allow the microcontroller 74 to control the operation of the IGP 14 in accordance with a selected operating program and stimulation parameters. In controlling the operation of the IGP 14, the microcontroller 74 is able to individually generate stimulus pulses at the electrodes 26 using the stimulation output circuitry 50, in combination with the control logic 52 and timer logic 56, thereby allowing each electrode 26 to be paired or grouped with other electrodes 26, including the monopolar case electrode, to control the polarity, amplitude, rate, pulse width and channel through which the current stimulus pulses are provided. The microcontroller 74 also performs the afore-mentioned shunt current compensation function, which will be described in further detail below.

The IGP 14 further comprises an alternating current (AC) receiving coil 84 for receiving programming data (e.g., the operating program and/or stimulation parameters) from the RC 16 and/or CP 18 in an appropriate modulated carrier signal, and charging and forward telemetry circuitry 86 for demodulating the carrier signal it receives through the AC receiving coil 84 to recover the programming data, which programming data is then stored within the memory 80, or within other memory elements (not shown) distributed throughout the IGP 14.

The IGP 14 further comprises back telemetry circuitry 88 and an alternating current (AC) transmission coil 90 for sending informational data sensed through the monitoring circuitry 70 to the RC 16 and/or CP 18. The back telemetry features of the IGP 14 also allow its status to be checked. For example, when the RC 16 and/or CP 18 initiates a programming session with the IGP 14, the capacity of the battery is telemetered, so that the RC 16 and/or CP 18 can calculate the estimated time to recharge. Any changes made to the current stimulus parameters are confirmed through back telemetry, thereby assuring that such changes have been correctly received and implemented within the implant system. Moreover, upon interrogation by the RC 16 and/or CP 18, all programmable settings stored within the IGP 14 may be uploaded to the RC 16 and/or CP 18.

The IGP 14 further comprises a rechargeable power source 92 and power circuits 94 for providing the operating power to the IGP 14. The rechargeable power source 92 may, e.g., comprise a lithium-ion or lithium-ion polymer battery. The rechargeable battery 92 provides an unregulated voltage to the power circuits 94 (e.g., 3V). The power circuits 94, in turn, generate the various voltages 96, some of which are regulated and some of which are not, as needed by the various circuits located within the IGP 14.

The rechargeable power source 92 is recharged using rectified AC power (or DC power converted from AC power through other means, e.g., efficient AC-to-DC converter circuits, also known as "inverter circuits") received by the AC receiving coil 84. To recharge the power source 92, the external charger 22 (shown in FIG. 4), which generates the AC magnetic field, is placed against, or otherwise adjacent, to the patient's skin over the implanted IGP 14. The AC magnetic field emitted by the external charger induces AC currents in the AC receiving coil 84. The charging and forward telemetry circuitry 86 rectifies the AC current to produce DC current, which is used to charge the power source 92. While the AC receiving coil 84 is described as being used for both wirelessly receiving communications (e.g., programming and control data) and charging energy from the external device, it should be appreciated that the AC receiving coil 84 can be arranged as a dedicated charging coil, while another coil, such as coil 90, can be used for bi-directional telemetry.

Additional details concerning the above-described and other IPGs may be found in U.S. Pat. No. 6,516,227, U.S. Patent Publication No. 2003/0139781, and U.S. patent application Ser. No. 11/138,632, entitled "Low Power Loss Current Digital-to-Analog Converter Used in an Implantable Pulse Generator," which are expressly incorporated herein by reference. It should be noted that rather than an IPG, the system 10 may alternatively utilize an implantable receiver-stimulator (not shown) connected to leads 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the stimulation in accordance with the control signals.

The IGP 14 may compensate for the current flowing through the shunt capacitances in any one of a variety of manners. In one embodiment, the memory 80 stores a differential equation that is a function of the shunt capacitance and the programmed electrical current value for each of the electrodes 26, and the microcontroller 74 computes the value of the electrical current generated by the electrical current source/sink based on the differential equation. For example, the model illustrated in FIG. 2 yields the following equation: $I=(R1)(C1)(R_t)(C2)(di_t(t)^2/dt^2)+(R1C1+R_t(C1+C2))(di_t/dt)+i_t(t)$. If the desired tissue current $i_t$ can be defined for therapeutic purpose (the programmed current value will equal the tissue current $i_t$), the microcontroller 74 can directly compute the value of the drive current I that will ultimately be used to obtain the desired tissue current $i_t$. Practical consideration must be taken into account as step changes in voltage or the slope of voltage at the tissue load in FIG. 2 would require impulse outputs from the current source E1, which require instantaneous infinite amplitude and power. Therefore target stimulation waveform can only be FIG. 3 can only be approximated at the tissue load in practice.

Figure 1:
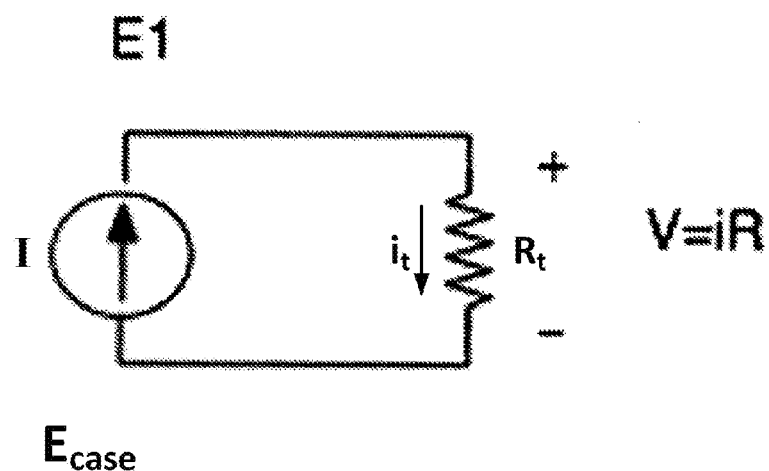
FIG. 1 is a circuit diagram of a prior art ideal electrode-tissue circuit.
Figure 2:
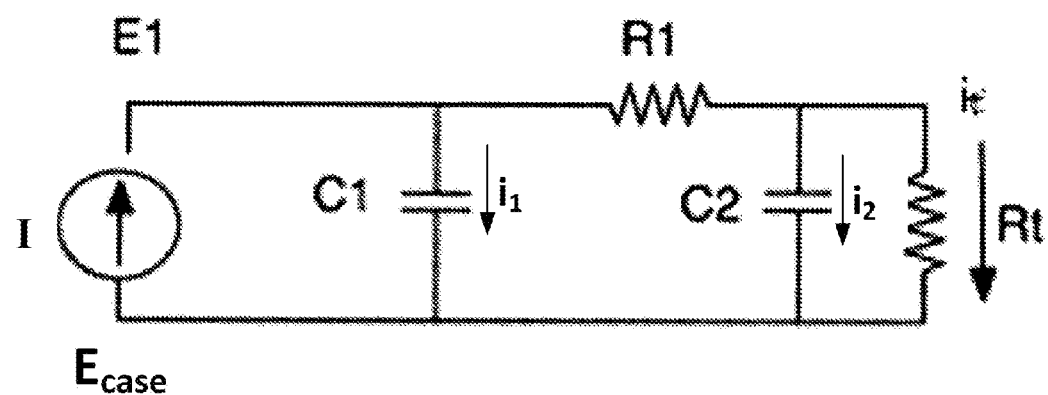
FIG. 2 is a circuit diagram of a prior art electrode-tissue circuit having parasitic circuit elements.
Figure 3:
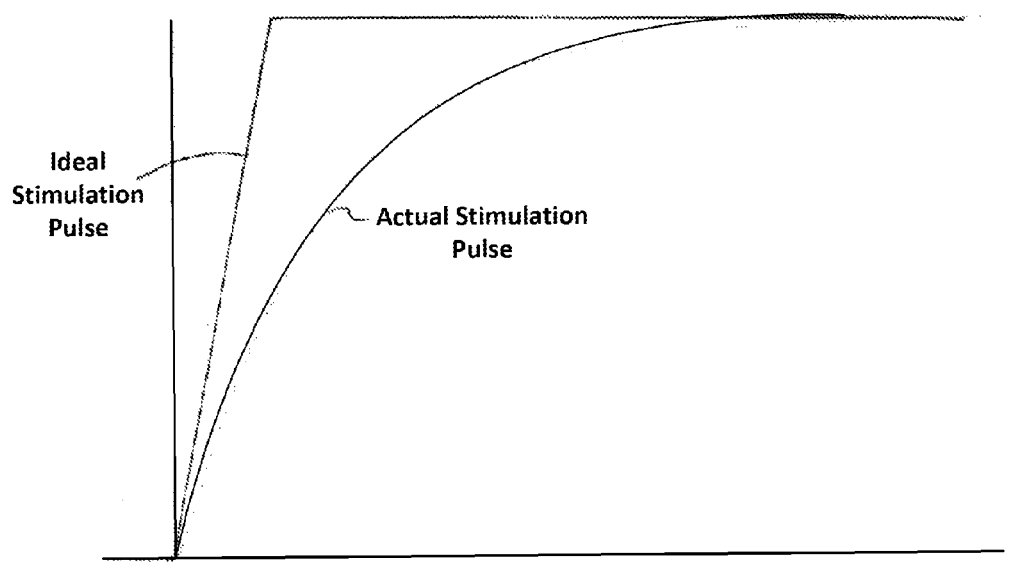
FIG. 3 is a timing diagram of an ideal electrical pulse generated by the electrode-tissue circuit of FIG. 1 versus an actual electrical pulse generated by the electrode-tissue circuit of FIG. 2.
Figure 9:
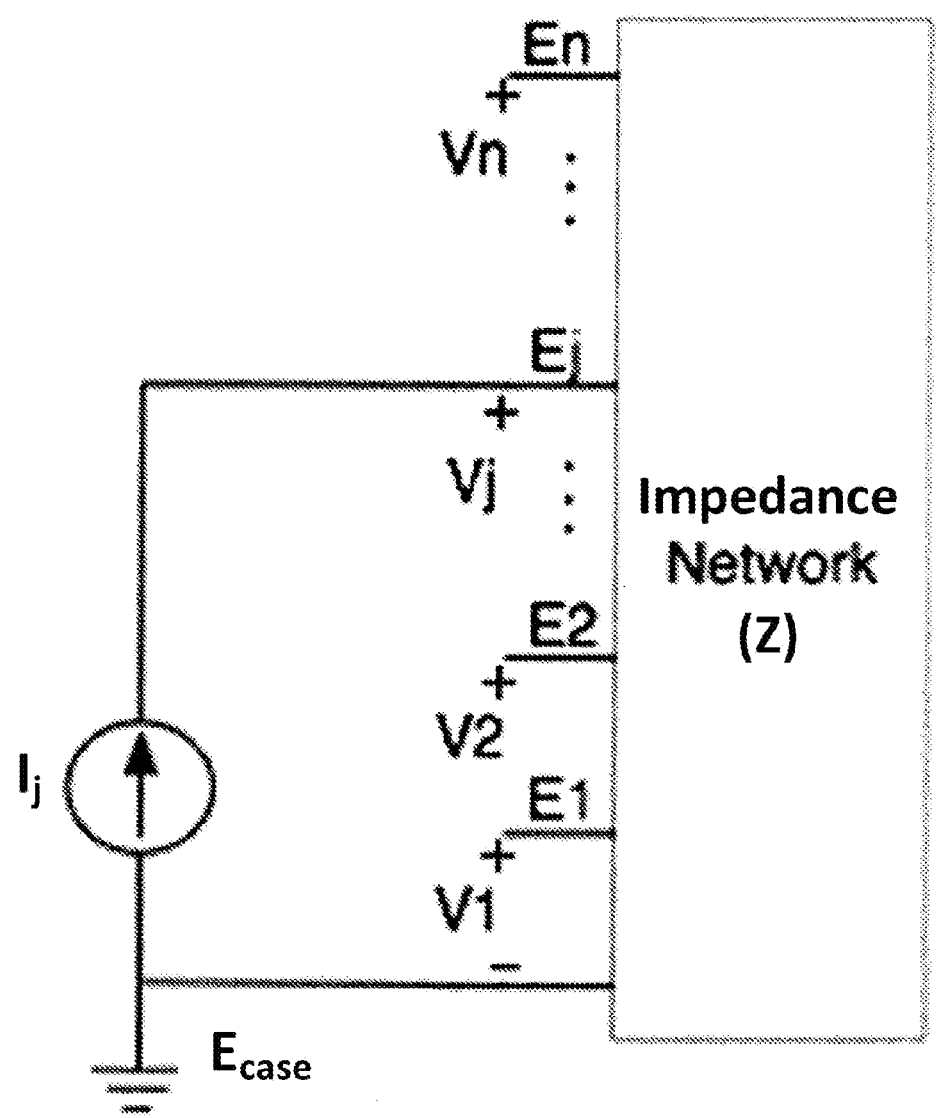
FIG. 9 is a circuit diagram of an electrical model of a multi-electrode system having an impedance network coupling the electrodes together, wherein the electrical model can be used by the IPG of FIG. 6 to compensate for shunting currents using a modeling technique.
Figure 10:
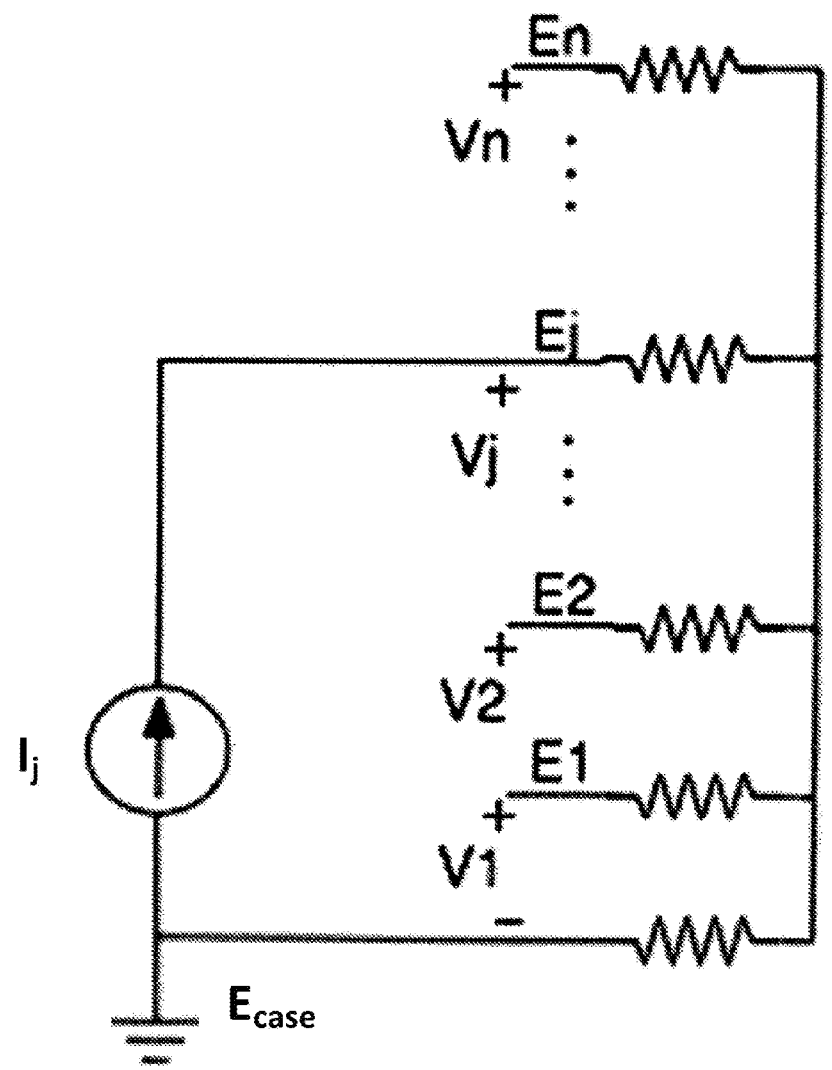
FIG. 10 is a circuit diagram of one embodiment of an impedance network that can be modeled in the multi-electrode system of FIG. 9.
Figure 11:
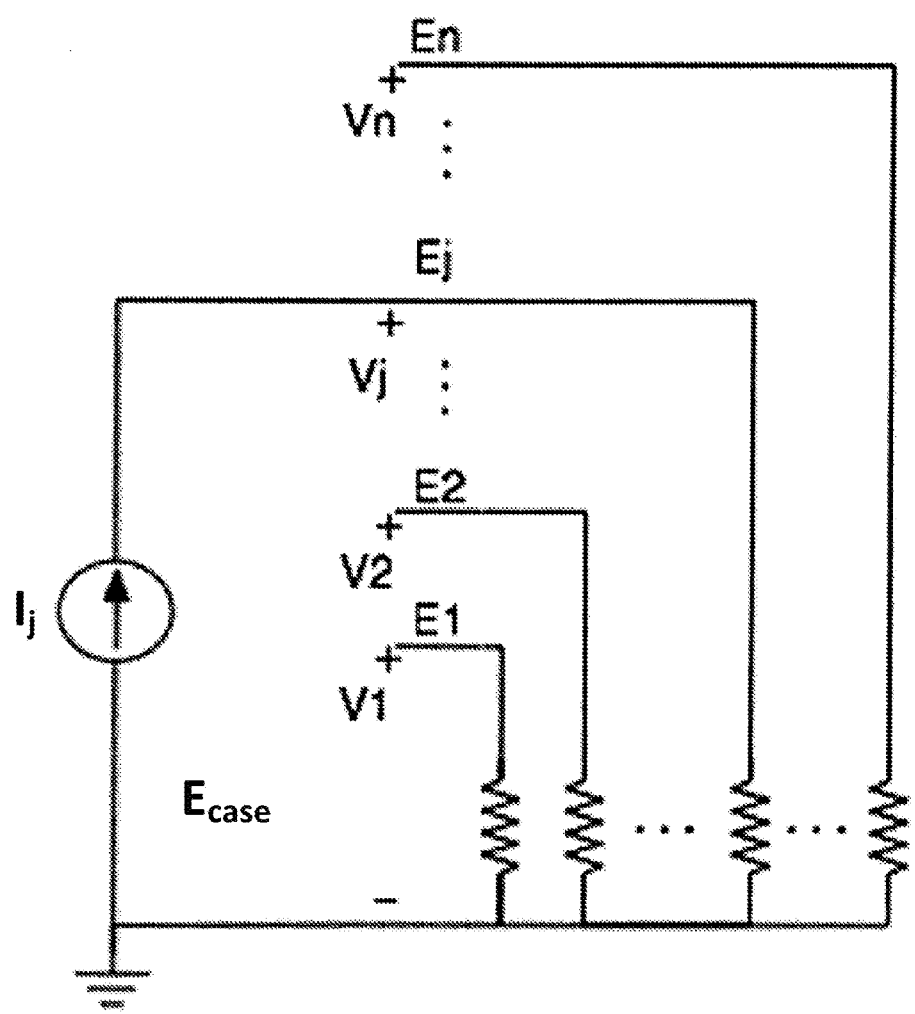
FIG. 11 is a circuit diagram of another embodiment of an impedance network that can be modeled in the multi-electrode system of FIG. 9.
Figure 12:
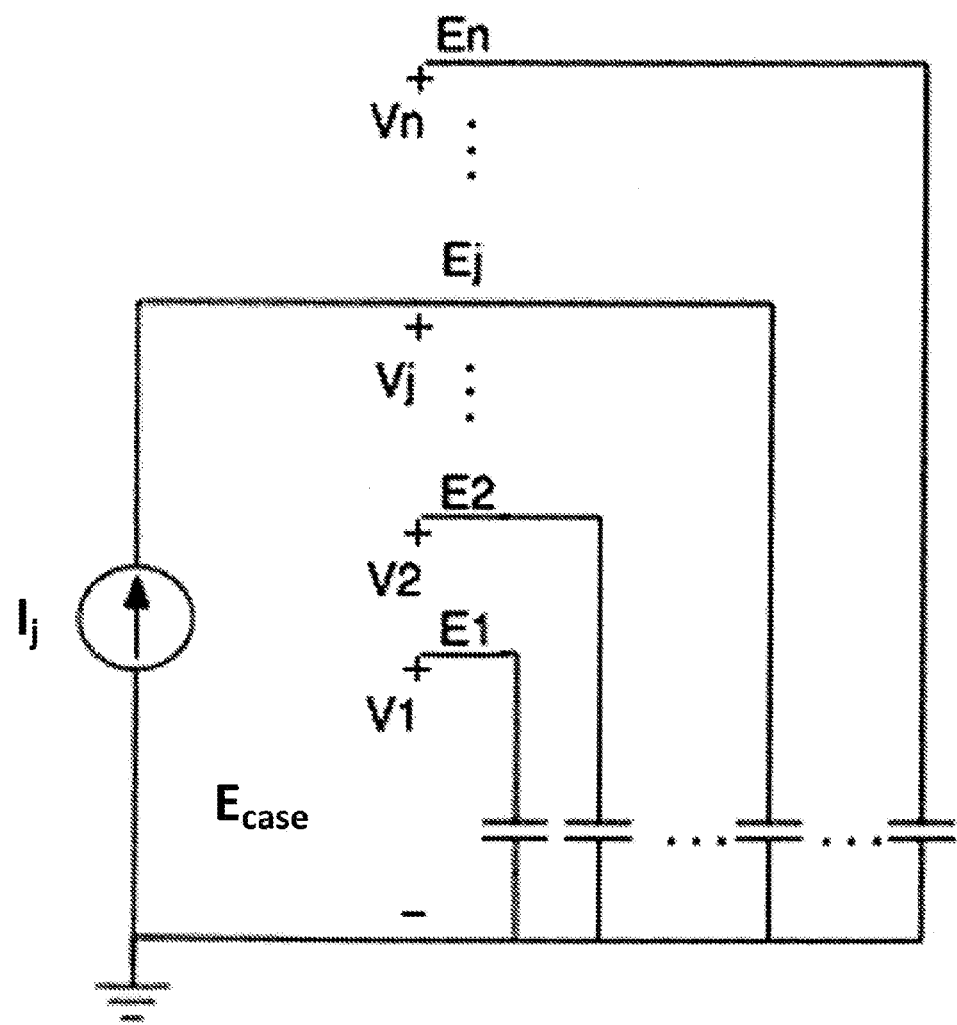
FIG. 12 is a circuit diagram of still another embodiment of an impedance network that can be modeled in the multi-electrode system of FIG. 9.

The two-electrode system illustrated in FIG. 2 has only one degree of freedom; that is, it is defined by one current source. However, as illustrated in FIG. 8, a neurostimulation system comprises many electrodes. Assuming the loads are linear, then the multi-electrode system can be described using the mathematical language of linear algebra and matrices. Referring to FIG. 9, consider a system with n lead electrodes E1-En and a case electrode $E_{case}$, and a linear impedance network coupling the electrodes together. The case electrode $E_{case}$ can be treated as a reference node from which all current is sourced and all voltages are measured. This system will interact with the tissue at n+1 points, but will only have n degrees of freedom. There is no loss of generality as any current or voltage between differing electrodes can be created by a superposition of currents and voltages with respect to the case electrode $E_{case}$. To describe this system electrically, the voltage at each electrode must be known as a function of current at the electrodes. To do this, a matrix Z representing the linear impedance network can be defined. This could be a model of the tissue impedance or any other linear load the IGP 14 experiences. The standard tissue impedance model can be represented by a parallel combination of resistors, as shown in FIG. 10, or alternatively, a parallel combination of resistors, as shown in FIG. 11. Or the tissue impedance model can be represented by a parallel combination of capacitors, as shown in FIG. 12, in which case, frequency dependent terms would be required in the entries of the matrix Z. Alternatively, differential operators could be used to reflect the fact that the change of the voltage is proportional to the relevant current.

The matrix Z has i, j entries having units of impedance that represents the ratio of the voltage on the $i_{th}$ electrode over the current being sourced into the $j_{th}$ electrode. If a current $I_j$ is injected into electrode $E_j$ (the $j_{th}$ electrode), this current will create voltages V1 through Vn on the respective electrodes E1 through En. These voltages can be zero if there is no effect. The matrix Z can be described as $Z=Z_{ij}$, where $Z_{ij}=V_i/I$. To determine the voltages $V_i$ given the current $I_j$ driving the impedance network $Z_{ij}$, the impedance network $Z_{ij}$ must be multiplied by the current column vector $I_j$ in accordance with the following equation $V_i=Z_{ij}\cdot I_j$, where · represents matrix multiplication.

The matrix Z defined above describes the voltage $V_i$ given an input of the current $I_j$. However, in order to compute the value of the drive currents required to set the tissue current at the programmed current, the drive current $I_j$ needs to be known as a function of voltage $V_i$. This can be obtained for non-singular matrices by taking the matrix inverse $I=Z^{-1}\cdot V$, where $Z^{-1}$ is the inverse of the impedance network matrix Z.

Figure 13:
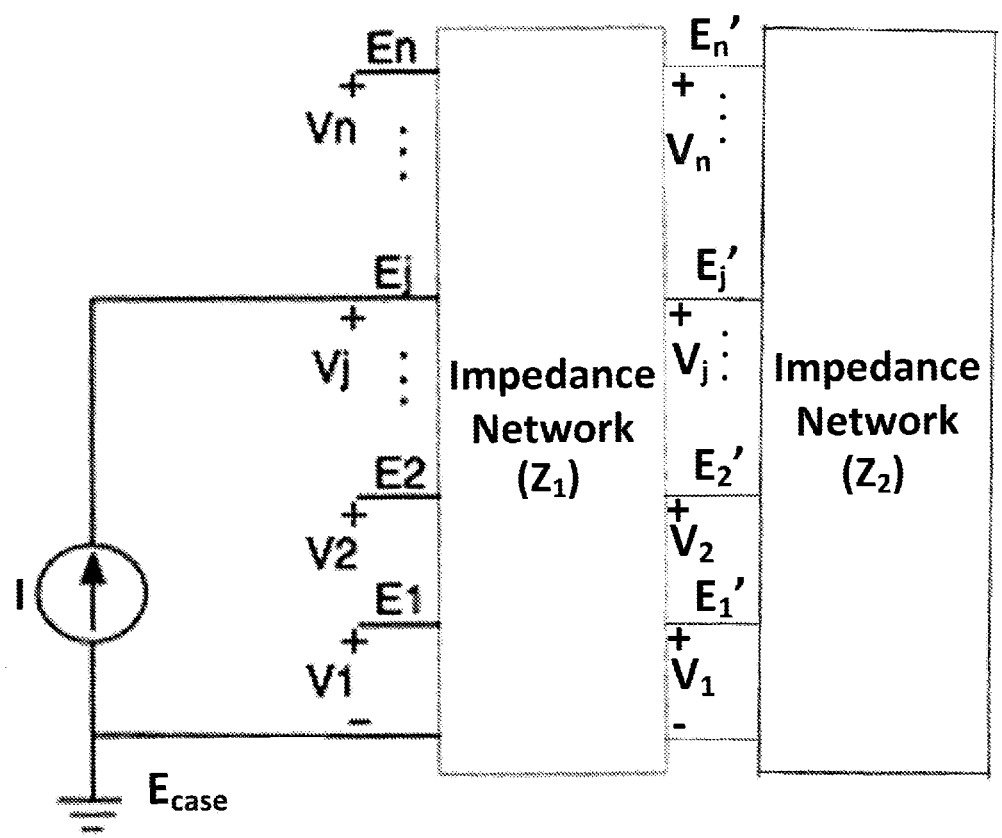
FIG. 13 is a circuit diagram of an electrical model of a multi-electrode system having two parallel impedance networks coupling the electrodes together.

Two impedance networks $Z_1$ and $Z_2$ can be placed in parallel, as illustrated in FIG. 13. That is, the voltage at the $i_{th}$ electrodes are the same, and the current at the $j_{th}$ electrodes are shared between the networks $Z_1$ and $Z_2$. Current can be shared even if no current is being driven into the networks by the IGP 14 at the $j_{th}$ electrodes. In this case, the current will just sum to zero. Thus, the voltages V1-Vn that the IGP 14 sees driving current I1-In into two parallel networks $Z_1$ and $Z_2$ and the currents $i_1$ and $i_2$ into the networks $Z_1$ and $Z_2$ can be computed as follows:

$$V=Z_1\cdot i_1=Z_2\cdot i_2; I=i_1+i_2 \Rightarrow$$

$$i_1=(Z_2^{-1}Z_1+I)^{-1}\cdot I;$$

$$i_2=(Z_1^{-1}Z_2+I)^{-1}\cdot I;$$

$$I=(Z_2^{-1}Z_1+I)^{-1}\cdot i_1;$$

$$V=Z_1(Z_2^{-1}Z_1+I)^{-1}\cdot I;$$

where I is the identity matrix.

Figure 14:
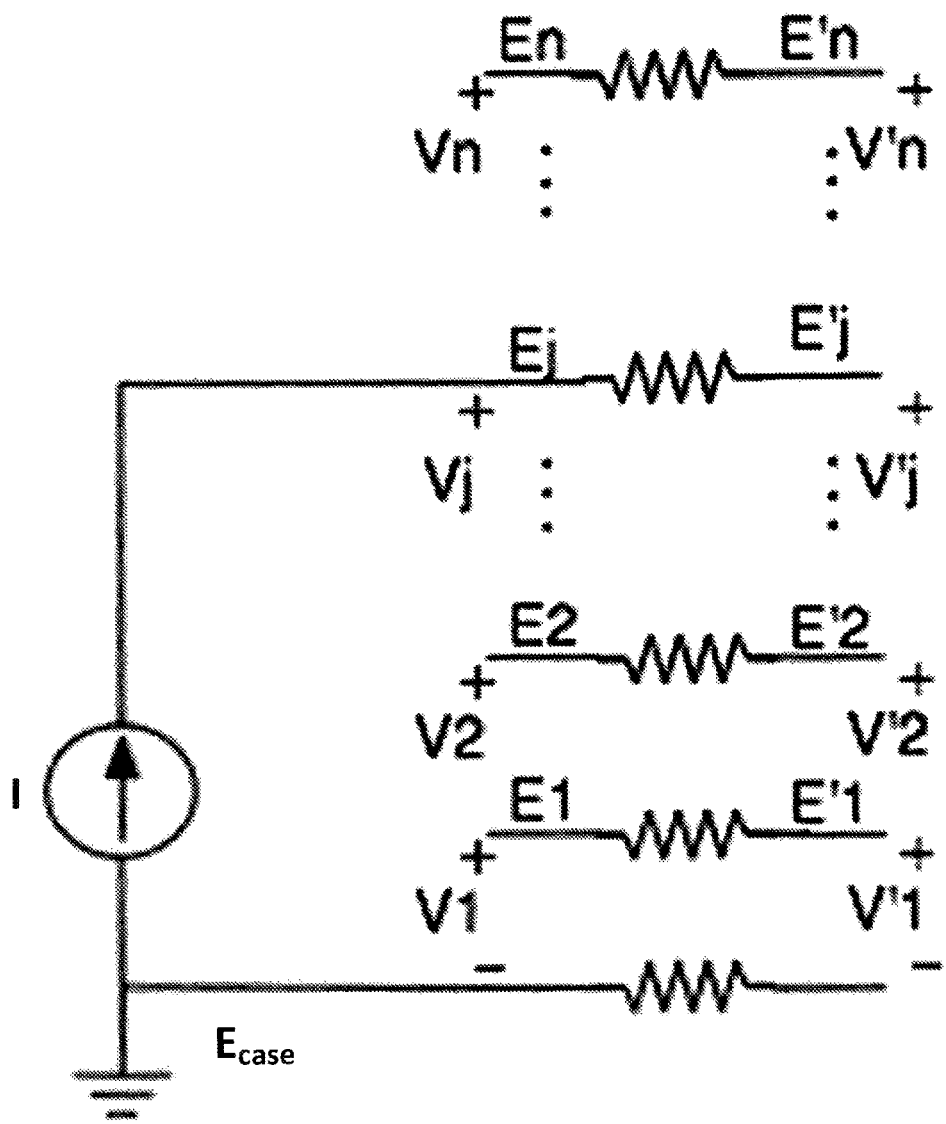
FIG. 14 is a circuit diagram of an electrical model of a multi-electrode system having a series impedance network coupling the electrodes together.

In addition to parallel impedance networks, series impedance loads also must be considered. These series impedance loads are similar to parallel impedance networks, except they are assumed to maintain the current at each electrode index the same while the voltages at each electrode index vary. These series impedance loads consist of 2n electrode; an n number of electrodes at one group of terminals, and another n number of electrodes at another group of terminals, as illustrated in FIG. 14. To determine the voltages V1-Vn at the terminals E1-En of IPG current drive input, not only the impedance matrix that describes the impedance of the network must be known, but voltages V'1-V'n on the other terminals E'1-E'n must be known. The voltage V1-Vn using matrix equations may be computed in accordance with the following: $V=Z\cdot i+V'$, where Z represents the series impedance.

Figure 15:
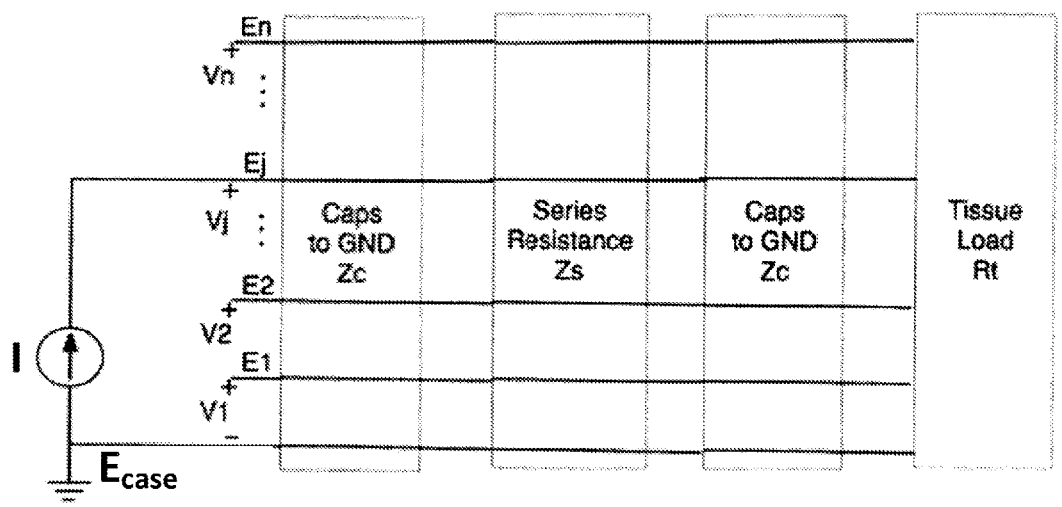
FIG. 15 is a circuit diagram of an electrical model of a multi-electrode system incorporating the electrode-tissue circuit of FIG. 2.

The multi-electrode equivalent model illustrated in FIG. 2 can be reconstructed using a combination of parallel and series impedance networks combined together to create the model illustrated in FIG. 15. The IPG drive current vector I can be computed using the following equation: $I=Z_c^{-1}(Z_t+Z_c(I+Z_c^{-1}Z_t)+Z_s(I+Z_c^{-1}Z_t))\cdot i$, where i is the tissue current vector and I is the IPG source current vector. It can be appreciated that the IPG drive current vector I is specified in terms of the desired tissue current vector i. Due to the capacitors, the time varying solution for I will be given by a linear differential equation. As in the two-electrode example illustrated in FIG. 2, an instantaneous finite change in the tissue current will demand impulses of current from the IPG electronics, which in practice can only be approximated.

In another embodiment in which the IGP 14 may compensate for the current flowing through the shunt capacitances using a direct measurement technique. In particular, the monitoring circuitry 70 (or alternatively, some other sensing device (not shown)) may measure a change in the voltage at each of the electrodes 26 during the delivery of the electrical pulse, and the microcontroller 74 computes the magnitude and polarity of electrical current flowing through each of the electrodes 26 based on the respective measured voltage changes and known capacitance values, and directing the current sources 62/64 to compensate for the absorbed or injected charge by generating an electrical current having the same magnitude and opposite polarity of the electrical current flowing through each electrode 26 in addition to the programmed electrical current value for each electrode 26.

Figure 16:
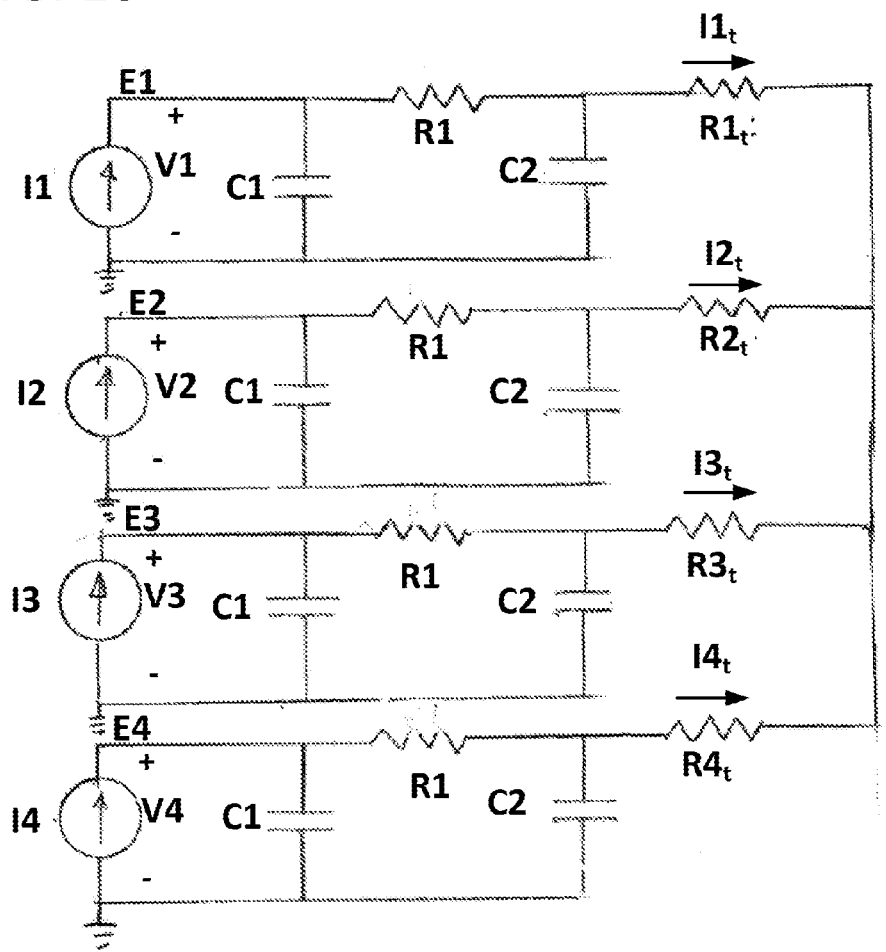
FIG. 16 is a circuit diagram of a multi-electrode system incorporating the electrode-tissue circuit of FIG. 2, wherein the IPG of FIG. 6 can use to compensate for shunting currents using a direct measurement technique.

For example, as illustrated in FIG. 16, a circuit may have four electrodes E1-E4 and four independent current sources I1-I4, where like in FIG. 2, C1, R1, and C2 represent lumped element models of the parasitic components of the neurostimulation lead, and any shunt capacitances in EMI filters and internal stimulation circuitry associated with each of the electrodes E1-E4. Thus, for each of the electrodes E1-E4, current will leak through the shunt capacitances C1 and C2 in response to changes in the voltage across these capacitances, preventing the specified electrical drive currents I1-I4 from reaching the tissue resistances, modeled as $R1_r$-$R4_r$. Instead, currents $i1_r$-$i4_r$ respectively flow through the tissue resistances $R1_r$-$R4_r$. In this example, current sources I1 and I4 are programmed to be active and current sources I2 and I3 are programmed to be inactive. That is, the current source I1 is programmed with an anodic current of a specified non-zero value, the current source I4 is programmed with a cathodic current of the same, but oppositely polarized, specified non-zero value, and the current sources I2 and I3 are each programmed with a zero current value.

Figure 17:
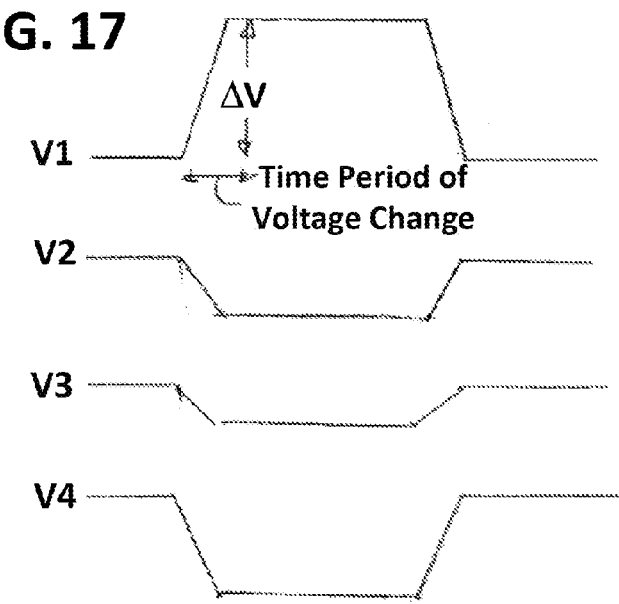
FIG. 17 is a timing diagram of the voltages respectively measured at the electrodes E1-E4 of the multi-electrode system illustrated in FIG. 16.

As illustrated in FIG. 17, electrical pulses respectively having voltages V1-V4 are delivered to the tissue resistances $R1_r$-$R4_r$. As can be appreciated, during the time periods when the voltage changes ΔV across the tissue resistances $R1_r$-$R4_r$ occur, current will be shunted through the capacitances, requiring compensation during each pulse in order to substantially match the programmed electrical currents for each of the electrodes E1-E4 to the actual electrical current delivered to each of the electrodes E1-E4. To perform the compensation function, the voltage across each of current sources is measured during changes in the voltages V1-V4. For example, the voltages V1-V4 may be measured at the beginning and end of the rising edge of the pulse and/or the beginning and end of the falling edge of the pulse to acquire the voltage changes ΔV across the tissue resistances $R1_r$-$R4_r$.

The average current $i1_r$-$i4_r$ though each of the tissue resistances $R1_r$-$R4_r$ during the time period in which the voltages V1-V4 change can then be computed in accordance with the equation i=C*dV/dt (where i is the current flowing through the respective tissue resistance, C is the shunt capacitance value associated with the electrode, and dV/dt is the rate of change of voltage across the respective tissue resistance). The compensating currents for the electrodes E1-E4 can then be computed by subtracting the average currents $i1_r$-$i4_r$ through the respective tissue resistance $R1_r$-$R4_r$ from the current values programmed for the respective electrode E1-E4, and then adding the compensating currents to the programmed current values to obtain the corrected values of the current to be delivered by the respective current sources I1-I4. The corrected current values for the respective current sources I1-I4 will then be used during the corresponding voltage varying periods of the next pulse. For any subsequent pulses, the computed currents flowing through the respective tissue resistance $R1_r$-$R4_r$ are compared to the newly corrected current values for respective current sources I1-I4, and the compensating currents are then added to the newly corrected current values for respective current sources I1-I4 to obtain the next corrected current values for the respective current sources I1-I4.

For example, if electrode E1 has been programmed to be +2 mA, electrode E4 has been programmed to be −2 mA, the average current $i1_r$ flowing through the tissue resistance $R1_r$ is +1.8 mA during the rising edge of the pulse, and the average current $i4_r$ flowing through the tissue resistance $R2_r$ is −1.4 mA during the rising edge of the pulse, the compensating currents for electrodes E1 and E4 will be +0.2 mA and −0.6 mA, respectively. Thus, the current sources I1 and I4 will be adjusted to generate electrical current values of +2.2 mA and −2.6 mA, respectively, thereby at least partially cancelling out the shunting currents associated with electrodes E1 and E4. For the inactive electrodes E2 and E3, if the average current $i2_r$ flowing through the tissue resistance $R2_r$ is −0.3 mA during the rising edge of the pulse, and the average current $i3_r$ flowing through the tissue resistance $R3_r$ is −0.1 mA during the rising edge of the pulse, the compensating currents for electrodes E2 and E3 will be +0.3 mA and +0.1 mA, respectively. Thus, the current sources I2 and I3 will be adjusted to generate electrical current values of +0.3 mA and +0.1 mA, respectively, thereby at least partially cancelling out the shunting currents associated with electrodes E2 and E3.

If during the next electrical pulse, the average current $i1_t$ flowing through the tissue resistance $R1_t$ is +1.9 mA during the rising edge of the pulse, and the average current $i2_t$ flowing through the tissue resistance $R1_t$ is −1.9 mA during the rising edge of the pulse, the compensating currents for electrodes E1 and E4 will be +0.1 mA and −0.1 mA, respectively. Thus, the current sources I1 and I4 will be adjusted by adding these compensating currents to the previously corrected electrical current values of +2.2 mA and −2.6 mA to generate the next corrected electrical current values of +2.3 mA and −2.7 mA, respectively, thereby at least partially cancelling out the shunting currents associated with electrodes E1 and E4. For the inactive electrodes E2 and E3, if the average current $i2_t$ flowing through the tissue resistance $R2_t$ is −0.1 mA during the rising edge of the pulse, and the average current $i3_t$ flowing through the tissue resistance $R3_t$ is +0.1 mA during the rising edge of the pulse, the compensating currents for electrodes E2 and E3 will be +0.1 mA and −0.1 mA, respectively. Thus, the current sources I2 and I3 will be adjusted by adding these compensating currents to the previously corrected electrical current values of +0.3 mA and +0.1 mA to generate the next corrected electrical current values of +0.4 mA and 0.0 mA, respectively, thereby at least partially cancelling out the shunting currents associated with electrodes E2 and E3.

Although the shunted current has been described as being iteratively compensated for on a pulse-by-pulse basis, the shunted current can be iteratively compensated for within an electrical pulse. For example, an electrical pulse may be divided into sixteen time intervals, with the measurement, compensating current computation, and current correction functions being performed individually on each time interval the same way as it was done previously on the pulse as a whole. The electrical pulse need not be divided into equal time intervals. For example, if the system can be approximated by a first order system and the intended electrical pulse is square, then it may only be necessary to divide the electrical pulse in to two time intervals with the first one being very short.

Although the compensating currents have been described as being directly added to the previously corrected current values to obtain the next corrected current values to be delivered by the respective current sources I1-I4, it should be appreciated that any appropriate function of the compensating currents can be added to the previously corrected current values. For example, the compensating currents may be integrated over time and multiplied by an appropriate gain (which may be 1 or some other value) prior to addition to the respective corrected values, thereby reducing DC errors, or differentiated over time and multiplied by an appropriate gain prior to addition to the respective correct values, thereby reducing overshooting. As another example, a moving average function, a mean function, or a FIR function may be performed on the compensating currents prior to addition to the corrected current values.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A neurostimulation device, comprising:
   a plurality of electrical terminals configured for being respectively coupled to a plurality of stimulation electrodes implanted within tissue of a patient;
   stimulation output circuitry configured for delivering time-varying electrical current to at least one of the stimulation electrodes via at least one of the electrical terminals to stimulate the tissue of the patient, the stimulation output circuitry including a shunt capacitance coupled to the at least one of the stimulation electrodes via the at least one of the electrical terminals that would, without compensation, absorb charge from or inject charge into the tissue in response to time-varying changes in the delivered time-varying electrical current, thereby causing an uncompensated electrical waveform to be delivered to the tissue adjacent the at least one of the stimulation electrodes, wherein the uncompensated electrical waveform deviates from a desired electrical waveform; and
   a controller configured for directing the stimulation output circuitry to at least partially compensate for the absorbed or injected charge, thereby causing a compensated electrical waveform to be delivered to the tissue adjacent the at least one of the stimulation electrodes, wherein the compensated electrical waveform matches the desired electrical waveform more closely than the uncompensated electrical waveform matches the desired electrical waveform.

2. The neurostimulation device of claim 1, wherein a characteristic between the uncompensated electrical waveform and the desired electrical waveform has a first error value, and the same characteristic between the compensated electrical waveform and the desired electrical waveform has a second error value less than the first error value.

3. The neurostimulation device of claim 2, wherein the characteristic is a total electrical charge over a period of time.

4. The neurostimulation device of claim 2, wherein the characteristic is a magnitude of an electrical current in a period of time.

5. The neurostimulation device of claim 4, wherein the electrical current is an average electrical current over the period of time.

6. The neurostimulation device of claim 2, wherein the characteristic is a waveform shape.

7. The neurostimulation device of claim 1, wherein the delivered time-varying electrical current comprises pulsed electrical energy having an electrical pulse having a rising edge and a falling edge, wherein the shunt capacitance would, without compensation, absorb charge from the tissue in response to a rising edge of the electrical pulse, and inject charge into the tissue in response to a falling edge of the electrical pulse.

8. The neurostimulation device of claim 1, wherein the controller is configured for directing the stimulation output circuitry to at least partially compensate for the absorbed or injected charge by actively injecting charge into the shunt capacitance when the shunt capacitance would, without compensation, remove charge from the tissue, and/or actively removing charge from the shunt capacitance when the shunt capacitance would, without compensation, inject charge into the tissue.

9. The neurostimulation device of claim 1, wherein the stimulation output circuitry comprises an electrical source configured for being coupled to the at least one of the stimulation electrodes via the at least one of the electrical terminals, and wherein the controller is configured for directing the electrical source to at least partially compensate for the absorbed or injected charge by generating an electrical current.

10. The neurostimulation device of claim 9, wherein the electrical source has an arbitrary pulse shaping capability that is configured to be controlled by the controller.

11. The neurostimulation device of claim 9, further comprising a processor configured for computing a value of the electrical current generated by the electrical source based on a differential equation that is a function of the shunt capacitance and a desired electrical current value.

12. The neurostimulation device of claim 9, further comprising:
    a sensing device configured for measuring a change in a voltage at the at least one of the stimulation electrodes during the delivery of the time-varying electrical current; and
    a processor configured for computing a magnitude and a polarity of electrical current flowing through the tissue adjacent the at least one of the stimulation electrodes based on a measured voltage change, computing a magnitude and a polarity of a compensating electrical current based on the computed magnitude and polarity of the electrical current flowing through the tissue adjacent the at least one of the stimulation electrodes and a desired electrical current value, and adding a function of the magnitude and polarity of the compensating electrical current to the desired electrical current value to obtain a magnitude and polarity of the electrical current that the controller directs the electrical source to generate.

13. The neurostimulation device of claim 12, wherein the function is one of a gain, a differentiation of the compensating electrical current over time multiplied by a gain, or an integration of the compensating electrical current over time multiplied by a gain.

14. A neurostimulation system comprising:
the neurostimulation device of claim 1;
at least one neurostimulation lead having the plurality of stimulation electrodes configured for being implanted within the tissue of the patient; and
the shunt capacitance coupled to the at least one of the stimulation electrodes.

15. The neurostimulation system of claim 14, wherein a characteristic between the uncompensated electrical waveform and the desired electrical waveform has a first error value, and the same characteristic between the compensated electrical waveform and the desired electrical waveform has a second error value less than the first error value.

16. The neurostimulation system of claim 15, wherein the characteristic is a total electrical charge over a period of time.

17. The neurostimulation system of claim 15, wherein the characteristic is a magnitude of an electrical current in a period of time.

18. The neurostimulation system of claim 17, wherein the electrical current is an average electrical current over the period of time.

19. The neurostimulation system of claim 15, wherein the characteristic is a waveform shape.

20. The neurostimulation system of claim 14, wherein the delivered time-varying electrical stimulation current comprises pulsed electrical energy having an electrical pulse having a rising edge and a falling edge, wherein the shunt capacitance would, without compensation, absorb charge from the tissue in response to a rising edge of the electrical pulse, and inject charge into the tissue in response to a falling edge of the electrical pulse.

* * * * *